(12) United States Patent
Jansen

(10) Patent No.: US 9,427,710 B2
(45) Date of Patent: Aug. 30, 2016

(54) RADIAL FILTRATION VENT AND MEDICAL DEVICE PACKAGING

(71) Applicant: Christopher Rene Jansen, Kaukauna, WI (US)

(72) Inventor: Christopher Rene Jansen, Kaukauna, WI (US)

(73) Assignee: Bemis Company, Inc., Neenah, WI (US)

( * ) Notice: Subject to any disclaimer, the term of this patent is extended or adjusted under 35 U.S.C. 154(b) by 0 days.

(21) Appl. No.: 13/840,558

(22) Filed: Mar. 15, 2013

(65) Prior Publication Data

US 2014/0262894 A1    Sep. 18, 2014

(51) Int. Cl.

| | | |
|---|---|---|
| *B01D 53/22* | (2006.01) | |
| *B01D 69/12* | (2006.01) | |
| *B01D 71/48* | (2006.01) | |
| *A61M 5/00* | (2006.01) | |
| *B01D 71/26* | (2006.01) | |
| *B01D 71/54* | (2006.01) | |

(52) U.S. Cl.
CPC .............. *B01D 69/12* (2013.01); *A61M 5/002* (2013.01); *B01D 53/22* (2013.01); *B01D 71/26* (2013.01); *B01D 71/48* (2013.01); *B01D 71/54* (2013.01); *B01D 2279/35* (2013.01)

(58) Field of Classification Search
USPC ....... 55/385.4, 364, 376, 486, DIG. 39, 367, 55/369; 95/5, 6, 15, 16; 493/186, 214; 604/332, 333; 251/262; 383/61.3, 97; 206/306, 363, 204, 438, 439
See application file for complete search history.

(56) References Cited

U.S. PATENT DOCUMENTS

| | | |
|---|---|---|
| 3,175,025 A | 3/1965 | Geen et al. |
| 3,503,497 A | 3/1970 | Rely et al. |
| 3,608,815 A | 9/1971 | Bunch |
| 3,655,503 A | 4/1972 | Stanley et al. |
| 3,782,083 A | 1/1974 | Rosenberg |
| 3,932,153 A | 1/1976 | Byrns |
| 3,953,566 A | 4/1976 | Gore |

(Continued)

FOREIGN PATENT DOCUMENTS

| | | |
|---|---|---|
| CA | 947678 A1 | 5/1974 |
| EP | 0785066 A2 | 1/1996 |

(Continued)

OTHER PUBLICATIONS

Technical Products Group, Technical Product Function Sheet "Foamex Cushioning Functions", retrieved Apr. 3, 2013 at http://www.qualityfoam.com/docs/foamex-cushioning-foam.pdf.

(Continued)

*Primary Examiner* — Duane Smith
*Assistant Examiner* — Minh-Chau Pham
(74) *Attorney, Agent, or Firm* — Sheena E. Conners

(57) ABSTRACT

A gas sterilization package component having (a) a gas diversion wall stock for at least a portion of a container, the wall stock having an opening therethrough; (b) a gas diversion layer; (c) a filter sheet disposed between (a) and (b), the filter sheet having a first surface and an opposing second surface circumscribed by a perimeter edge; and wherein the first surface of the filter sheet is attached to a surface of said gas diversion layer and the second surface of the filter sheet is sealed to a surface of the wall stock whereby an opening in the wall stock is covered by the filter sheet and a gas passageway is defined from the opening through a portion of the second surface of the filter sheet and extending through said filter perimeter edge.

26 Claims, 5 Drawing Sheets

(56) References Cited

U.S. PATENT DOCUMENTS

| | | | |
|---|---|---|---|
| 4,022,324 A | 5/1977 | Schuster | |
| 4,058,632 A | 11/1977 | Evans et al. | |
| 4,091,922 A * | 5/1978 | Egler | A61M 25/002 206/306 |
| 4,187,390 A | 2/1980 | Gore | |
| 4,189,519 A | 2/1980 | Ticknor | |
| 4,203,520 A | 5/1980 | Schuster | |
| 4,252,846 A | 2/1981 | Romesberg et al. | |
| 4,270,658 A * | 6/1981 | Schuster | A61B 19/026 206/439 |
| 4,296,862 A | 10/1981 | Armentrout et al. | |
| 4,356,012 A * | 10/1982 | Hofstetter | 55/385.4 |
| 4,395,254 A | 7/1983 | Schuster | |
| 4,449,970 A * | 5/1984 | Bevan et al. | 604/333 |
| 4,461,420 A * | 7/1984 | Horvath | B65D 81/24 206/439 |
| 4,470,153 A * | 9/1984 | Kenan | B65D 31/02 206/439 |
| 4,482,053 A | 11/1984 | Alpern et al. | |
| 4,550,141 A | 10/1985 | Hoh | |
| 4,550,546 A | 11/1985 | Raley et al. | |
| 4,615,926 A | 10/1986 | Hsu et al. | |
| 4,666,778 A | 5/1987 | Hwo | |
| 4,714,595 A * | 12/1987 | Anthony et al. | 422/294 |
| 4,778,058 A | 10/1988 | Yamazaki et al. | |
| 4,783,321 A * | 11/1988 | Spence | 422/300 |
| 4,784,885 A | 11/1988 | Carespodi | |
| 4,834,245 A | 5/1989 | Ohga et al. | |
| 4,874,090 A * | 10/1989 | Dyke | A61B 19/026 206/439 |
| 4,875,587 A | 10/1989 | Lulham et al. | |
| 4,875,899 A * | 10/1989 | Holtermann | 604/333 |
| 4,882,229 A | 11/1989 | Hwo | |
| 4,903,841 A | 2/1990 | Ohsima et al. | |
| 4,916,190 A | 4/1990 | Hwo | |
| 4,937,139 A | 6/1990 | Genske et al. | |
| 4,938,750 A * | 7/1990 | Leise, Jr. | 604/333 |
| 4,944,409 A | 7/1990 | Busche et al. | |
| 4,945,125 A | 7/1990 | Dillon et al. | |
| 4,957,518 A * | 9/1990 | Brassell | 96/4 |
| 4,957,522 A * | 9/1990 | Brassell | 96/4 |
| 5,023,121 A | 6/1991 | Pockat et al. | |
| 5,034,422 A | 7/1991 | Triolo et al. | |
| 5,066,683 A | 11/1991 | Dillon et al. | |
| 5,128,414 A | 7/1992 | Hwo | |
| 5,157,058 A | 10/1992 | Dillon et al. | |
| 5,195,527 A | 3/1993 | Hicks | |
| 5,342,673 A | 8/1994 | Bowman et al. | |
| 5,362,553 A | 11/1994 | Dillon et al. | |
| 5,547,752 A | 8/1996 | Yanidis | |
| 5,590,777 A * | 1/1997 | Weiss | A61B 19/026 206/439 |
| 5,613,779 A | 3/1997 | Niwa | |
| 5,626,569 A * | 5/1997 | Holtermann et al. | 604/333 |
| 5,653,090 A * | 8/1997 | Weiss | A61B 19/026 206/439 |
| 5,720,789 A * | 2/1998 | Pinson | 55/364 |
| 5,725,645 A * | 3/1998 | Wickland et al. | 96/17 |
| 5,762,797 A | 6/1998 | Patrick et al. | |
| 5,868,244 A * | 2/1999 | Ivanov et al. | 206/63.3 |
| 5,947,287 A * | 9/1999 | Weiss | A61B 19/026 206/439 |
| 5,968,459 A | 10/1999 | Nalepa et al. | |
| 5,988,489 A | 11/1999 | Moteki et al. | |
| 5,997,968 A | 12/1999 | Dries et al. | |
| 6,102,571 A | 8/2000 | Moteki et al. | |
| 6,106,448 A | 8/2000 | Obara et al. | |
| 6,131,573 A | 10/2000 | Brown | |
| 6,136,878 A | 10/2000 | Free et al. | |
| 6,177,036 B1 | 1/2001 | Van Der Hoeven et al. | |
| 6,196,708 B1 | 3/2001 | Rogers | |
| 6,319,481 B1 | 11/2001 | Banks | |
| 6,355,078 B1 * | 3/2002 | Wickland | 55/385.4 |
| 6,468,482 B1 | 10/2002 | Frieze et al. | |
| 6,476,137 B1 | 11/2002 | Longo | |
| 6,541,086 B2 | 4/2003 | Moteki et al. | |
| 6,551,608 B2 | 4/2003 | Yao | |
| 6,589,477 B1 | 7/2003 | Frieze et al. | |
| 6,594,971 B1 | 7/2003 | Addy et al. | |
| 6,808,908 B2 | 10/2004 | Yao et al. | |
| 6,841,586 B2 | 1/2005 | Free et al. | |
| 6,969,197 B2 * | 11/2005 | Sedley | A61L 2/26 206/438 |
| 7,431,157 B2 | 10/2008 | Porret et al. | |
| 7,470,062 B2 | 12/2008 | Moteki et al. | |
| 7,481,581 B2 | 1/2009 | Oshima et al. | |
| 7,595,032 B2 | 9/2009 | Banks | |
| 7,631,760 B2 * | 12/2009 | Guelzow | A61F 2/0095 206/204 |
| 7,713,320 B2 * | 5/2010 | Pham | 55/385.4 |
| 7,887,238 B2 | 2/2011 | Turvey et al. | |
| 7,938,580 B2 | 5/2011 | Gaskell et al. | |
| 7,985,343 B2 | 7/2011 | Haldopoulos et al. | |
| 8,056,719 B2 | 11/2011 | Porret et al. | |
| 8,083,823 B2 * | 12/2011 | Clerget | 55/385.4 |
| 8,187,534 B2 | 5/2012 | Mao | |
| 8,231,273 B2 | 7/2012 | Turvey et al. | |
| 8,418,872 B2 | 4/2013 | Smith | |
| 2003/0031857 A1 | 2/2003 | Saier | |
| 2003/0118491 A1 * | 6/2003 | Frieze et al. | 422/297 |
| 2003/0165663 A1 | 9/2003 | Christopherson et al. | |
| 2004/0129648 A1 | 7/2004 | Manesis | |
| 2005/0189252 A1 * | 9/2005 | Naylor | A61B 19/026 206/439 |
| 2008/0294007 A1 * | 11/2008 | Takada | 600/139 |
| 2009/0200198 A1 | 8/2009 | Guelzow et al. | |
| 2010/0028575 A1 | 2/2010 | Vanhamel | |
| 2010/0104845 A1 | 4/2010 | MacLennan et al. | |
| 2010/0154353 A1 | 6/2010 | Cesa et al. | |
| 2011/0079525 A1 | 4/2011 | Peck et al. | |
| 2011/0139650 A1 | 6/2011 | Dworak | |
| 2011/0152913 A1 * | 6/2011 | Jones et al. | 606/192 |
| 2011/0201050 A1 | 8/2011 | Niazi | |
| 2012/0267272 A1 * | 10/2012 | Agrawal | A61B 19/026 206/363 |
| 2015/0083627 A1 * | 3/2015 | Gorman | B65D 75/004 206/439 |

FOREIGN PATENT DOCUMENTS

| | | | | |
|---|---|---|---|---|
| EP | WO 2004/071308 A1 * | 8/2004 | | A61B 17/06 |
| EP | 1644098 A2 | 4/2006 | | |
| EP | 2057957 A1 | 5/2009 | | |
| EP | 2108381 A1 | 10/2009 | | |
| GB | 2485377 A | 5/2012 | | |
| WO | 9111374 A2 | 8/1991 | | |
| WO | 2009117328 A1 | 9/2009 | | |

OTHER PUBLICATIONS

UFP Technologies, "Reticulated Foam", retrived Apr. 3, 2013 at http://steplaw.com/reticulatedfoam.html.
POREX Technologies, "POREX® Porous PTFE Materials",retrieved online Oct. 29, 2012 at www.porex.com/technologies /applications/antimicrobial/.

* cited by examiner

RADIAL FILTRATION VENT AND MEDICAL DEVICE PACKAGING

BACKGROUND

1. Technical Field

The present application relates generally to gas sterilization packaging and more specifically to venting and filtration means for such packaging.

2. Background Information

Articles such as medical devices can be held within a container e.g. a pouch to protect the contents from microbial contamination, air, moisture, etc. The container is typically sealed to provide a barrier to microbes. The container may be a pouch with contents held between two sheets that form the pouch. Typically, disposable medical equipment and implantable devices are sterilized following packaging and before transport to healthcare providers. Common forms of sterilization include irradiation, autoclaving, and treatment with a sterilizing gas, such as ethylene oxide (ETO). In order to gas sterilize articles and maintain sterility, certain containers e.g. pouches are provided with a gas permeable membrane or wall which allows introduction and removal of a sterilizing gas such as ethylene oxide. This gas permeable wall also functions as a barrier to entry of pathogens such as bacteria, viruses and other microbes. Articles such as medical devices and tools e.g. artificial joints, stents, implantable structures and equipment, surgical knives, catheters, clamps, etc. may be stored and transported in a sterile condition until needed whereupon the contents may be accessed under controlled conditions to minimize infection and introduction of undesirable organisms. These sterilizable containers often use spunbonded polyolefin polymeric sheets such as Tyvek® as a permeable membrane wall component to permit gas sterilization and to act as a microbial barrier; see e.g. European Patent EP 0785066B.

Another typical medical device package has a sheet of breathable material sealed to the peripheral edge of a tray or flexible thermoformed blister container to form a lidding. After placing and sealing an article inside, a sterilizing gas is admitted into the interior of the package through the breathable membrane.

These existing types of packaging have several disadvantages. In particular, the commonly employed material Tyvek® spun bonded polyolefin is susceptible to weakened seals and failure due to the use of elevated temperatures and steam in gas sterilization. More careful and time consuming handling must be used to minimize seal failures which negatively impacts packaging productivity and limits the speed at which such packages can be manufactured. Opening of the package for use also raises potential problems. Use of nonwoven sheet material made of individual fibers that are thermally bonded to each other may potentially result in exposure to, or formation during an opening process, of small fibers that may be deposited on the sterilized article; this a particular concern where such nonwoven spunbonded polyolefin sheets are included as a wall component and form a peelable seam. Also, spunbonded nonwovens such as Tyvek® are expensive.

Accordingly, there is a need for a more cost and labor efficient method for the packaging and sterilization of catheters, stents and other medical devices and instruments medical devices and instruments. Also, it would be desirable to utilize gas sterilization in rigid containers where such containers are preferred or in applications where use of a flexible membrane material is undesirable. Furthermore, membrane materials such as paper or Tyvek® are not very breathable i.e. have low gas flow rates and can be either fragile as in the case of certain papers, or expensive. It would be advantageous to reduce the area size of a vent relative to known breathable membrane wall components presently employed in medical gas sterilization packages while maintaining or improving gas flow in the sterilization process without sacrificing antimicrobial barrier properties.

BRIEF SUMMARY

In one form of the present disclosure, a gas sterilization package component is provided having (a) a gas diversion wall stock for at least a portion of a container, the wall stock having an opening therethrough; (b) a gas diversion layer; and (c) a filter sheet disposed between (a) and (b), the filter sheet having a first surface and an opposing second surface circumscribed by a perimeter edge. The first surface of the filter sheet is attached to a surface of the gas diversion layer and the second surface of the filter sheet is sealed to a surface of the wall stock whereby an opening in the wall stock is covered by the filter sheet and a gas passageway is defined from the opening through a portion of the second surface of the filter sheet and extending through the filter perimeter edge or a distal portal area of said filter sheet. In this manner sterilizing gas may flow back and forth through the opening and the perimeter edge (or area proximate thereto) of the filter media without undue stresses on package walls and seals and the filter media may provide a tortuous path against ingress of microbes into contents held within a sterilized package.

DETAILED DESCRIPTION

Figure 1:
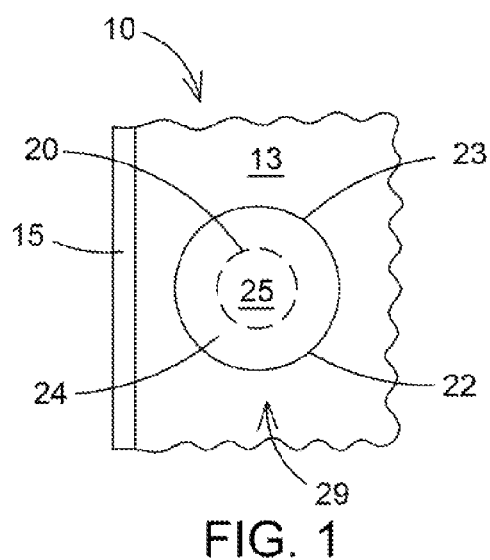
FIG. 1 is a plan view of a portion of a first side of a container having a radial filter vent in accordance with the present invention.

Porous materials such as Tyvek® spunbonded polyolefin sheets and medical grade paper are used for gas sterilization packaging. The gas permeability of these materials is such that it allows for flow of sterilant and flushing gases into and out of the package being sterilized. These materials maintain the sterility of the package as they prevent bacteria and other microbes from entering the package. However, Tyvek® is very expensive and paper does not typically have as good of a microbial barrier as Tyvek®.

According to filtration theory, the following five mechanisms contribute to the filtration efficiency of particles from a fluid stream by a filtration medium:
1. Interception—this occurs when a particle flows into direct contact with a part of the filter medium and becomes trapped.
2. Inertial Impaction—this occurs when a particle, due to its inertia, travels out of the flow path and contacts the filter medium.
3. Diffusion Impaction—this occurs when a particle is made to contact the filter medium due to kinetic energy from surrounding gas molecules.
4. Gravitational Settling—this occurs due to normal gravitation effects on a particle causing it to settle into contact with the filter medium.
5. Electrokinetic Effects—this is when electrostatic charge of a material attracts particles to a filter medium.

In porous medical device packaging systems, the porous material allows for proper gas flow, but can also be thought of as a filter medium in order to provide microbial barrier. In high flow situations, such as during pressure changes due to ascent and descent of an airplane, Interception and Inertial Impaction play a strong role in filtration. During low gas flow situations such as storage, Diffusion, Gravitational Effects, and Electrokinetic Effects play a prominent role in filtration. Tyvek® and paper depend upon all of these methods to create a sufficient microbial barrier. The tortuous path inherent in the structure of Tyvek® as well as its electrostatic properties make Tyvek® an excellent microbial barrier for packaging medical devices. However, Tyvek® is not extremely permeable to gas and thus requires a large surface area to allow for a sufficient volume of gas flowing at a high enough rate to efficiently sterilize while preventing package rupture during pressure changes in the sterilization cycles, and to allow for efficient removal of sterilant gases. In the present invention, a novel vent design utilizes a change in flow direction with a predominant transverse or cross-directional flow through a filter medium which permits use of other filter media. This results in an adequate or improved microbial barrier through one or more of the following mechanisms:
1. Interception—a longer travel distance than the 2 to 8 mils typical with gas flow across the thickness of paper or Tyvek, results in more filter medium surfaces to intercept particles.
2. Inertial Impaction—the initial perpendicular change in flow direction should create flow disturbances, which in turn create inertia and cause particles to escape the flow stream. Additionally, a long, tortuous path creates more opportunities for contact with the filter medium. This tortuous path may be longer than that found in the prior art without reducing gas flow rates; indeed improved gas flow rates may be provided by the invention.
3. Diffusion Impaction—since the surface area at the edge of the inventive radial vent may be selected to be greater than the surface area of the port or opening in the large area facial surface (which opening is present only on one side of the filter medium, the flow rate may decrease and become much slower as gas traverses the material in its radial directions (i.e. transverse or cross-directional to the sheet thickness), allowing for more diffusion impactions as the velocity changes in transit.
4. Gravitational Settling—gravitational effects, especially during storage periods, will cause particles to fall towards the bottom layer of the vent which is preferably sealed and so become trapped.
5. Electrokinetic Effects—certain materials, such as polytetraflouroethylene (PTFE) which have a high capacity for static charge, can be used as the filter medium.

Since the filtration efficiency, and thus microbial barrier are improved with this design, more permeable materials can be used as the porous medium. Examples of more permeable structures are open cell foams, sintered porous plastics, high loft nonwoven fabrics, and woven fabrics. Since these materials are more permeable, less surface area of material is required over or as part of a package wall. Since Tyvek® is typically the most expensive material in a packaging system, these alternate materials may be less expensive than Tyvek®, and a reduction in porous surface area required should allow for a reduction in overall cost. Additionally, since the overall porous surface area on the package has been reduced, exposure of the environment to a porous surface area is reduced and, concomitantly, potential for contamination is reduced. The novel radial vent design should allow for both a cost reduction, increased gas flow rates, reduced stress on package seals, and an improvement in package microbial barrier, and thus, patient safety.

In the present invention, a novel gas sterilization package component is provided which typically comprises: a microbial filtration, gas vent having (a) a first apertured gas diversion wall layer having an opening of area "A", (b) a second gas diversion layer having a nonapertured area greater than "A" and overlaying the first wall opening, and (c) a filtration media sheet disposed between and connecting layers (a) and (b).

By "gas diversion layer" is meant a layer which is sufficiently restrictive to air flow through its thickness that air flow is diverted transversely i.e. radially or perpendicular to the filter media sheet thickness. Preferably, the predominate gas flow into and out of the novel vent is caused to turn 90° which permits a gas transit distant greater than the thickness of the filter media sheet.

Suitable materials which may be selected and used for gas diversion layers include many of the same materials that may be used to construct a typical container wall and may be monolayer or multilayer in construction. Examples of such materials include polyolefins, polyethylene terephthalates, polyamides, nylons, polystyrenes, polyacrylates, generally any polymer that is known for use in flexible polymer packaging. Such materials may be homopolymers, copolymers, and there derivatives and blends thereof. Metal foils and metalized films are also contemplated. One or more functional properties may be contributed by one or more layers including desired levels of heat sealability, optical properties e.g. transparency, gloss, haze, abrasion resistance, coefficient of friction, tensile strength, flex crack resistance, puncture resistance, abrasion resistance, printability, colorfastness, flexibility, stretch or shrinkability, dimensional stability, barrier properties to gases such as oxygen, or to moisture, light of broad or narrow spectrum including e.g. uv resistance, etc. Preferred materials for use as container walls, pouch films, lidstock, and gas diversion layers include nylons, polyesters, polystyrenic polymers, and polyolefin e.g ethylene or propylene homopolymers or copolymers, or mixtures thereof in any number of layers, particularly, but not limited to, one to nine or 14 layers or more . . . preferred polyolefins include ethylene homopolymers or copolymers and may include low, medium, high and ultra-low or ultra-high density polymers. Examples are high density polyethylene (HDPE), ethylene alpha-olefin copolymers (EAO) preferably utilizing butene-1, hexene-1, or octene-1 comonomer with a predominate ethylene comonomer portion) and including e.g. linear low density polyethylene (LLDPE), very low density polyethylene (VLDPE), plastomers, elastomers, low density polyethylene (LDPE) copolymers of ethylene and polar groups such as vinyl acetate or ethyl acrylate e.g. ethylene vinyl acetate (EVA) or ethylene methyl acrylate (EMA) or ethylene acrylic acid copolymer (EAA), functional group modified polyers including e.g. anhydride modified EAOs. Propylene homopolymers and copolymers including polypropylene and propylene ethylene copolymer are useful. Gas diversion or container wall structures may also include a metal foil and may be a metal foil laminate with metal foil and a polymeric layer such as nylon. It may also be a metal foil laminate with an outer layer of polyethylene terephthalate, a core layer of metal foil and an inner layer of polyethylene. In this arrangement, the polyethylene terephthalate layer serves as a protective layer to the foil, and the polyethylene layer facilitates sealing. The foil is an excellent barrier to materials organisms, oxygen, moisture and light.

Gas diversion layers in accordance with the present invention may utilize a gas barrier layer such as aluminum foil, polyvinylidene chloride copolymers such as saran, or ethylene vinyl alcohol copolymers which provide high barriers to gas permeability or materials such as nylon which impede gas permeation to a lesser extent, or materials such as polyethylene which are generally not considered oxygen barriers. However, the key property of these layers is that the flow of gas through the material is impeded or blocked to an extent sufficient that gas flow will follow an alternative path presented by the choice of filter media. Depending upon the filter media selected the relative ease of transmission across the thickness of the diversion layer to the alternate gas passageway presented transversely i.e. radially through the filter media sheet will vary. It may be determined without undue experimentation for the desired combination of materials. For example, it is preferred that a nonperforated, noncellular thermoplastic layer be used as the diversion layers such as polyester. However, medical grade paper or a spunbonded, coated or uncoated Tyvek® may also be used. In these cases the small surface area of the diversion layer distal to the package wall means that (a) the high resistance to gas flow across paper or Tyvek® and (b) the relatively low resistance of the radial gas passageway through the filter media will cause a sufficient diversion of gas radially to increase the gas flow greatly in excess e.g. many times that achievable by the use of Tyvek® or paper alone. A suitable alternative to adhesive or fusion attachment of a separate diversion layer is contemplated in which the filter media surface or surfaces are themselves fused or welded to close its open pore structure to block or otherwise greatly diminish gas flow therethrough except at the required facial opening and distal end portions. Similarly, these surfaces may also be sealed or blocked by the use of chemical, adhesive, or irradiative means.

Adhesives useful in the present invention include permanent adhesives and pressure sensitive adhesives commonly available from many commercial sources. It is contemplated that acrylic and anhydride modified polymers may be employed as well as many adhesives which may be selected depending upon other material selections for the filter material as well as the gas diversion layer materials.

Additives and processing aides; natural and synthetic colorants, pigments and dyes; fillers such as calcium carbonate or carbon black, antimicrobial agents.

According to the present invention a filtration media is used to provide gas transport while inhibiting, reducing or preventing passage of small particles, foreign materials, viruses, and microbes.

Suitable filtration media sheets may be polymeric, cellulosic or non-cellulosic or a combination thereof. Suitable cellulosic materials include cotton, wood pulp such as fluff pulp and non-wood plant counterparts. Suitable non-cellulosic materials include thermoplastics that can be used to provide porous thermoplastic filter media sheets which include, but are not limited to, homopolymers and copolymers of polyolefins, polyurethanes, polyamides, nylons, polycarbonates, poly(ether sulfones), fluoropolymers such as polytetrafluoroethylene (PTFE) and polyvinylidene fluoride (PVDF), and mixtures thereof. A preferred thermoplastic is a polyolefin. Examples of suitable polyolefins include, but are not limited to: ethylene vinyl acetate; ethylene methyl acrylate; polyethylenes; polypropylenes; ethylene-propylene rubbers; ethylene-propylenediene rubbers; poly (l-butene); polystyrene; poly(2-butene); poly(l-pentene); poly(2-pentene); poly(3-methyl-1-pentene); poly(4-methyl-1-pentene); 1,2-poly-1,3-butadiene; 1,4-poly-1,3-butadiene; polyisoprene; polychloroprene; poly(vinyl acetate); poly(vinylidene chloride); and mixtures and derivatives thereof. A preferred polyolefin is polyethylene homopolymer or copolymer. Examples of suitable polyethylenes include, but are not limited to, low density polyethylene, high density polyethylene, ultra-high molecular weight polyethylene, ethylene alpha-olefin copolymers such as linear low density polyethylene or very low density polyethylene, and derivatives thereof. Suitable filter media sheets made of porous sintered thermoplastics such as polyolefins may be made from the materials and by the processes as more fully described in U.S. Pat. No. 6,551,608, U.S. Publication No. 2010/0104845, and EP 1 644 098 B1 each of which is hereby incorporated by reference in its entirety. Other filter media may include e.g. air laid, wet laid or dry laid nonwovens of materials such as polypropylene, polyethylene, polyester, nylon, cellulose or combinations thereof. Materials used in spirometer filters may be adapted for use e.g. air laid polypropylene fiber mats which are needle punch bonded to a polypropylene spunbonded point bonded web.

The filter media sheets may also be made from open celled foamed polymers. It has long been known that a "foam" of polyurethane can be prepared by reacting a polyisocyanate with a poly-hydroxy compound in the presence of a small amount of water which acts as a blowing agent. The water reacts with isocyanate groups producing carbon dioxide gas which forms small gas bubbles or cells in the "foam" when the polyurethane sets.

Such "foam" products have a structure made up of numerous individual cells which generally are constructed of a three dimensional skeletal structure of interconnected strands with membranes or windows joined to the skeletal structure such that they partition contiguous cells. The skeletal structure in these cellular materials is usually considerably thicker than the membranes or windows. When the foam windows are removed, an open-celled reticulated foam is produced which permits fluids to flow through the remaining skeletal structure. A method for producing reticulated foam is described in U.S. Pat. No. 3,175,025 to Geen. Commercially available open celled foamed polymers are available from many sources including UPF Technologies of Georgetown, Mass., U.S.A. Very fine cell polyurethane foam and processes for making the same are further described in U.S. Pat. Nos. 5,034,422 and 6,136,878.

The porous thermoplastic materials of the invention may further comprise materials such as lubricants, colorants, fillers, processing additives, and mixtures thereof. Suitable fillers include, but are not limited to: microcrystalline cellulose, cellulosic fibers, titanium dioxide, carbon black, siliceous fillers, polyethylene fibers and filaments, and mixtures thereof.

In addition, antimicrobial, anti-bacterial, anti-viral and anti-mycotic agents may be incorporated within the filter medium structure. Suitable agents include e.g., natural antimicrobial agents; polymeric antimicrobial agents; phenolic and chlorinated phenolic compounds; resorcinol and its derivatives; bisphenolic compounds; benzoic esters; halogenated carbanilides; thazolines; trichloromethylthioimides; metal salts; silver ions; and mixtures thereof as further described in U.S. Pat. No. 6,551,608.

Preferably, this filtration media is a microporous structure which may be e.g. a sintered thermoplastic e.g. sintered porous polyolefin e.g. an ultra high molecular weight polyethylene, or an open celled polymeric material such as those sold under the trademark Porex® by Porex Technologies GmbH of Aachen, Germany. Preferred materials are chemically inert, and have excellent physical properties including high tensile strength and temperature resistance to withstand elevated temperatures and steam employed in gas sterilization processes. Other desirable properties for preferred embodiments of the invention include filter media having oleophobic and hydrophobic properties and uniformity of pore size. Also, porous PTFE material which is an expanded polytetrafluoroethylene (PTFE) polymeric film is commercially available under the Porex trademark. Expanded polytetrafluoroethylene (PTFE) films are further described in U.S. Pat. Nos. 3,953,566; 4,187,390; 4,945,125; 5,066,683; 5,157,058; and 5,362,553 each of which is hereby incorporated by reference in their entireties. Expanded PTFE materials are also available commercially from Tetratec, Philadelphia, Pa. as Tetratec #1305 and from Sumitomo Electric Industries, Osaka, Japan under the brand Poreflon® WP-100. An expanded PTFE film typically comprises a plurality of nodes interconnected by fibrils to form a microporous structure.

Porous filter media according to the present invention have a preferred average pore size between about 1 to 500 microns. Advantageously, the pore size will preferably have substantial uniformity, although materials with a range of pore sizes are suitable. Preferred filter media such as sintered polymers from Porex are compatible with steam and ethylene oxide sterilization processes and may be ultrasonically welded or heat sealed.

Various materials may be used for the three essential layers of the radial filter vent layers and the container itself. Gurley Hill porosity values may be used to select the materials. "Gurley Hill porosity" refers to the air resistance of an approximately 6.45 cm$^2$ (1 in$^2$) circular area of test sample using a pressure differential of 1.22 kPa and is measured in accordance with International Standard ISO 5636-5, "Paper and board—Determination of air permeance and air resistance (medium range)—Part 5: Gurley method." Gurley Hill porosity values are reported in the amount of time (seconds) required for a given volume (100 cm$^3$) of air to pass through the test sample. In general, Gurley Hill porosity values indicate the gas barrier strength of a sample; lower values indicate the sample is more porous. Samples with Gurley Hill porosity values greater than 300 seconds are generally considered substantially non-breathable.

Figure 2:
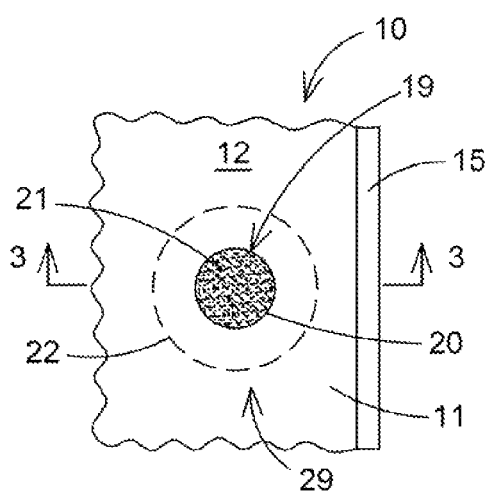
FIG. 2 is a plan view of the opposite side of the container portion of FIG. 1.
Figure 3:
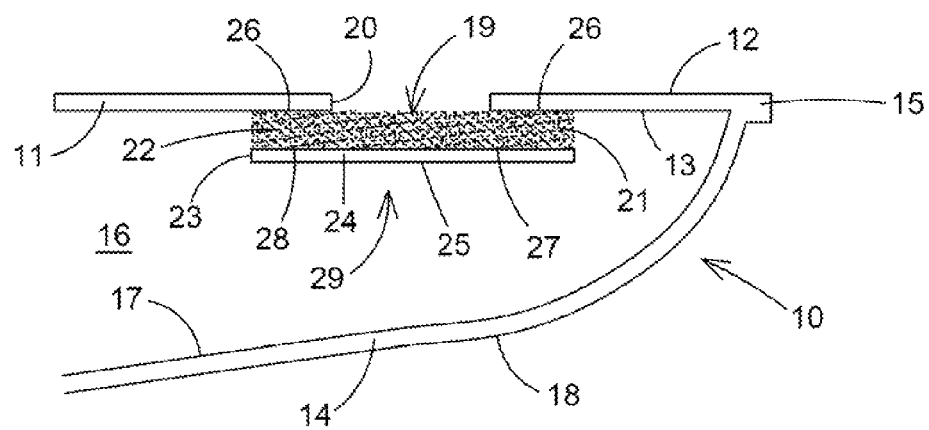
FIG. 3 is a sectional view of the container portion of FIG. 2.

Referring now to the Drawings, FIGS. 1, 2, and 3 represent an embodiment of the invention and illustrate a package container segment such as a pouch wall having a radial filter vent. In FIG. 2, a plan view of a container pouch segment 10 has a first panel 11 with an first panel surface 12 and an opposing first panel surface 13 (See FIGS. 1 and 3). FIG. 3 is a sectional view of FIG. 2 taken along lines 3-3 and as best seen in FIG. 3, first panel 11 is sealed to a second panel 14 by a perimeter seal 15 defining a perimeter of a compartment 16 which is bounded by first panel 11 and second panel 14 of the pouch 10. Preferably, the perimeter seal 15 can, for example, have a minimum width of about 1 mm to about 5 mm or more. Preferred widths are from 5 to 15 mm with a typical width being about 8-10 mm.

Second panel 14 has an interior surface 17 facing the pouch compartment 16 and an opposing exterior surface 18. The perimeter seal 15 may be either peelable or non-peelable. Advantageously, perimeter seal 15 is a peelable seal which is peelable along at least a portion of the seal or along the entire seal to provide access to the pouch contents.

Described herein are pouches that are equipped with a radial filter vent and preferred embodiments of such pouches may also advantageously provide easy access to remove contents within the pouch. The novel pouches may be manually opened without use of scissors or other tools, preferably using easy to peel open systems such as peelable seals. "Peelable seal" and like terminology is used herein to refer to a seal, and especially heat seals, which are engineered to be readily peelable without uncontrolled or random tearing or rupturing the packaging materials which may result in premature destruction of the package and/or inadvertent contamination or spillage of the contents of the package. A peelable seal is one that can be manually peeled apart to open the package at the seal without resort to a knife or other implement to tear or rupture the package. Many varieties of peelable seals are known in the art, such as those disclosed in U.S. Pat. No. 4,944,409 (Busche et al.); U.S. Pat. No. 4,875,587 (Lulham et al.); U.S. Pat. No. 3,655,503 (Stanley et al.); U.S. Pat. No. 4,058,632 (Evans et al.); U.S. Pat. No. 4,252,846 (Romesberg et al.); U.S. Pat. No. 4,615, 926 (Hsu et al.) U.S. Pat. No. 4,666,778 (Hwo); U.S. Pat. No. 4,784,885 (Carespodi); U.S. Pat. No. 4,882,229 (Hwo); U.S. Pat. No. 6,476,137 (Longo); U.S. Pat. No. 5,997,968 (Dries, et al.); U.S. Pat. No. 4,189,519 (Ticknor); U.S. Pat. No. 5,547,752 (Yanidis); U.S. Pat. No. 5,128,414 (Hwo); U.S. Pat. No. 5,023,121 (Pockat, et al.); U.S. Pat. No. 4,937,139 (Genske, et al.); U.S. Pat. No. 4,916,190 (Hwo); and U.S. Pat. No. 4,550,141 (Hoh), the disclosures of which are incorporated herein in their entirety by reference thereto.

A non-peelable seal may also be employed e.g. a strong integral heat seal along either a portion or along the entire perimeter. Such a non-peelable seal may be easily opened by tear open features such as notches, and surface weakened areas, or through the use of tools such as scissors, etc. Referring again to FIG. 2, first panel 11 has an opening 19 therethrough providing fluidic communication between the exterior of the package container and its interior so that gases may enter or exit the opening 19 which is defined by opening perimeter 20 through a filter 21. Filter 21 covers opening 19 extending past opening perimeter 20 on the interior side of the package container to an outer filter perimeter edge 22 shown in FIG. 2 by a dashed line. Referring now to FIG. 1, a plan view depicts the opposing side of the container segment 10 with the second panel removed. Thus in FIG. 1 the second panel surface 13 of first panel 11 of pouch segment 10 is shown having perimeter seal 15. A gas diversion layer 24 is sealed to the filter (see FIG. 3). The outer filter perimeter 22 coincides with an outer perimeter 23 of gas diversion layer 24. The gas diversion layer has an outer surface 25 which faces compartment 16 (See FIG. 3). First panel opening perimeter 20 is depicted in FIG. 1 by a dashed line. Referring again to FIG. 3, filter 21 is sealed to the first panel surface 13 at first filter surface 26 so that the filter covers opening 19 past opening perimeter 20 for a pre-determined distance before reaching the pouch compartment past the filter. This distance will coincide to either or both of the outer diversion layer perimeter 23 or outer filter perimeter 22. The path provides a tortuous gas passageway from the pouch exterior opening 19 through the filter 21 until reaching the interior compartment 16. Preferably this pre-determined distance is greater than the shortest distance across the thickness of the filter which would typically lie perpendicular from the first filter surface 26 adjacent opening 19 to a second filter surface 27 which has been sealed and blocked by gas diversion layer 24. The filter 21 is sealed to gas diversion layer 24 at an interface between the second filter surface 27 and an inner surface 28 of the gas diversion layer 24. The seals between (a) the filter 21 and the first panel, or (b) the filter 21 and the gas diversion layer 24 can be formed by a variety of ways, but is preferably a permanent seal. For example, the seal may be formed as a weld heat seal by application of heat and pressure to the first panel surface 13 and the first filter surface 26 with their respective surfaces in contact with each other for a sufficient time to cause bonding with cooling of the bonded perimeter to form an integral permanent seal. Alternatively, an adhesive can be sandwiched between the panel surface 13 of first panel 11 and the filter surface 26. Similarly, the seal (a) between the second filter surface 27 and gas diversion layer surface 28, as well as the seal (b) between the first and second panels 11, 14, respectively i.e. the perimeter seal 15, may be a permanent seal made by use of a heat seal or permanent adhesive. The perimeter seal 15, whether permanent or peelable, in combination with the first and second panels 11, 14 can seal contents within the compartment 16 with only a gas passageway that filters out unwanted materials such as particles and microbes. Thus, the pouch 10 is equipped with a gas sterilization package component 29 in the form of a radial filter vent which comprises a filter sheet disposed between a gas diversion layer and an apertured gas diversion wall stock, and so equipped provides a gas sterilization container and barrier to nongaseous particles including biological agents, pathogens, bacteria, viruses, etc., Furthermore, the radial filter vent and container when adapted with post-sterilization seals such as described in U.S. Pat. No. 7,938,580, which is hereby incorporated by reference in its entirety, may also provide a barrier to gases such as oxygen, moisture, ultraviolet light, etc. and provide a means for inclusion of gas and/or moisture scavenger materials e.g. in the form of a sachet. In the present invention because of the advantageous use of a very small dimensioned porous opening a simple means of final closure may be employed e.g. by use of a small heat seal or adhesive patch over the vent to provide a complete hermetic seal and barrier to light, moisture, etc.

Typical contents for various embodiments of the inventive container may include, for example, medical devices, stents, catheters, medical equipment, tools, bandages, surgical supplies, transdermal patches, bandages, wound care products as well as large bag filling e.g. for flour, feed, cement, sand, fertilizer, etc. The inventive vent and container may also find a variety of applications outside of the medical field where rapid venting due to pressure changes is required to equilibrate internal pressure within a package or other article with exterior pressures while achieving or maintaining a barrier to undesirable particles, chemicals, or organisms, etc.

Figure 4:
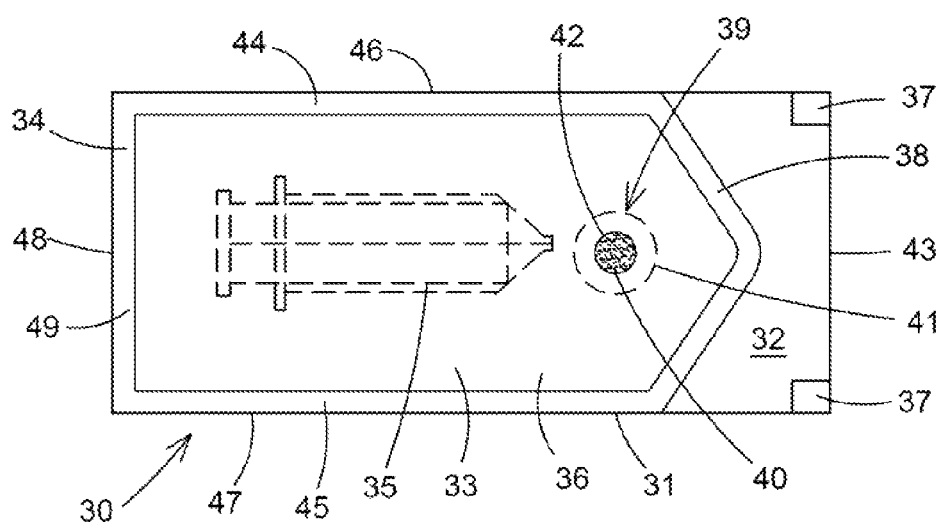
FIG. 4 is a plan view of a pouch having a radial filter vent in accordance with the present invention.

Referring now to FIG. 4, a container 30 in the form of a pouch in accordance with the present invention is shown having a container perimeter 31 with a header area 32 and compartment area 33. The compartment area 33 is defined by a compartment perimeter seal 34 and a medical apparatus 35 such as a syringe is depicted with dashed lines as being held within the compartment 33 formed by sealing a first plastic polymeric panel 36 to a second plastic polymeric panel (not shown) which the first panel overlays. Additional tacking seals 37 hold the first and second panels together in the header area 32, but allow for manual separation by peeling apart the compartment perimeter seal 34 which separates panel 36 from the overlaid second panel to provide access to the syringe apparatus 35. The seal 34 has a chevron design 38 adjacent the header area 32 to facilitate opening as the panels are separated beginning at the header area 32 and proceeding towards the compartment 33. The container 30 is equipped with a radial filter vent 39 which is similar to the vent depicted in FIGS. 1-3. The radial filter vent 39 has a microbial barrier filter 40 attached to an interior surface of the first panel 36 and the filter has an outer perimeter edge 41 within the compartment 33 depicted by a dashed line. An opening defined by opening perimeter 42 in first panel 36 provides access for a gas passageway between the exterior of the container 30 and its interior compartment 33 which is otherwise sealed against gas passage. On the far side of the filter 40 distal from the filter side adjacent the opening and first panel, this distal filter surface, which is similar to filter surface 27 in FIG. 3, is sealed by a gas diversion layer (not shown) so that gas may only exchange through fluidic communication between the exterior and interior of the container by following a tortuous path. This path extends between the opening defined by opening perimeter 42 and the filter perimeter edge 41 and proceeds through the tortuous path of the filter's interior. Apart from the filter edge 41 and the opening in the first panel, both of the filter's surfaces are sealed against gas flow by the first panel which is sealed to the filter media proximate the opening, and by a distal gas diversion layer adjacent and sealed to an opposing side of the filter media.

Furthermore, the container pouch 30 may have inner surfaces of the respective first and overlaid panels each comprising a layer that has a low interaction with the pouch's intended contents e.g. a drug eluting stent or chemical coated apparatus and may be substantially chemically inert and/or resist scalping of contents. The contents 35 are illustrated in FIG. 4 as a dashed line to illustrate that the contents 35 are within the pouch 30.

The first panel 36 and the overlaid second panel can be made from the same materials or different materials. Furthermore, the first and second panels can be a multilayered or laminated structure. The structure may be a single layer or a plurality of layers which may be polymeric, metallic, sheets, films or foils or combinations thereof. For example, the first and second panels can have a metal foil layer that forms an intermediate or core layer inside of either or both of the first and second panels and one or more polymer layers that form the inside and/or outside surface of the pouch 30. The metal foil layer can be aluminum. The one or more polymer layers can include cellulosic or preferably noncellulosic polymers, homopolymers or copolymers, blends of polymers. The panels may be constructed of one or more materials which contribute specific functionality to the package. Examples of suitable materials for one or more of these layers include polymers or copolymers such as polyethylene terephthalate, polyolefins e.g. polyethylene, polyester, nylon, styrenic polymers, cyclic polyolefins, metal foils, metalized films, oxygen or moisture barrier polymers such as ethylene vinyl alcohol copolymers, polyacrylonitriles, and vinylidene chloride copolymers such as saran. For example, a polyethylene layer can be sandwiched between a polyethylene terephthalate layer and the foil layer. The pouch 30 can further have a sealant layer that forms the inside surface of the compartment 33 such that an oxygen and/or moisture and/or uv light barrier layer such as the metal foil layer can be sandwiched between the sealant layer and the one or more polymer layers. The sealant layer can include polyethylene, ionomer, polyacrylonitrile, polyester, Barex®, or Surlyn®. The laminate may include more layers than those described above such as an adhesive layer between the sealant layer and the foil layer to adhere the sealant layer to the foil layer. Advantageously, sealants such as adhesives may be pattern applied. The thickness of the multilayer structure laminate may be any suitable thickness that provides structural integrity, and desired combinations of properties which may vary depending upon the nature of the contents, usage requirements and which may include e.g. consideration of barrier properties, abuse resistance, heat resistance, heat sealability, scalping resistance, puncture resistance, abrasion resistance, optical properties, haze, gloss, printability, transparency, as may be determined by those skilled in the art in view of the present disclosure. It is expected that typical preferred thicknesses, for example, may be advantageously employed between about 50 μm and about 200 μm.

In the example, illustrated in FIG. 4, the pouch 30, absent its contents, is relatively flat and forms a rectangular shape, and the radial filter vent is somewhat flat, relatively small and circular, but it will be recognized that many different shapes for both the container 30 and radial filter vent 39 may be employed including polygons such as hexagons or circular or oval or other curved or linear shapes or combinations thereof may be used as well as flexible, semi-rigid or rigid containers or combinations thereof.

To illustrate use of the container by a packager or manufacturer of articles to be contained with the inventive package, the radial filter vent containing package is assembled with tack seals 37 at opposing ends of first container pouch side 43, and a chevron first seal 38 extending into respective second and third parallel seal portions 44, 45 which are adjacent respective opposing second and third container sides 46, 47. A fourth side 48 opposing first side 43 is left open to compartment 33 to permit insertion of contents into the container 30 which after insertion may then be sealed along fourth side 48 with fourth seal 49 which extends from second seal portion 44 to opposing third seal portion 45 and thereby forms a sealed microbe barrier ventable package about compartment 33 by sealing together the first panel 36 and overlaid second panel having a continuous compartment perimeter seal 34 formed by seal portions 38, 44, 45, and 49 leaving only a tortuous path gas vent microbial barrier passageway between the exterior and interior thereof via radial filter vent 39.

Figures 5, 6:
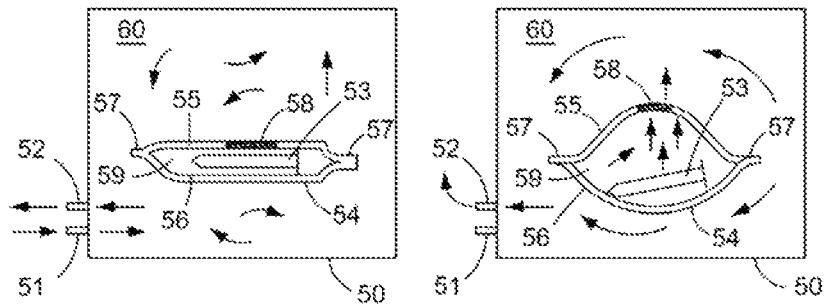
FIG. 5 is a schematic view of a gas sterilization chamber containing a vented pouch under ambient pressure.
FIG. 6 is a schematic view of the chamber of FIG. 5 under vacuum.

Referring now to FIGS. 5 and 6, both of which are schematic drawings depicting a gas sterilization chamber 50 having gas ingress means such as ingress port 51 and gas egress means such as egress port 52. Within the chamber 50 is an article represented by a medical device such as a syringe 53 in a container represented by pouch 54 having an upper first panel wall 55 and a lower second panel wall 56 sealed about a perimeter of the pouch 54 by perimeter seal 57 producing an airtight seal, but for a filter vent 58 which provides gaseous communication between an interior compartment 59 and an external environment 60 outside the pouch 54. The closed headed arrows represent air flow.

In a typical or representative gas sterilization process, a sealed package such as pouch 54 containing an article to be sterilized such as a syringe 53 is placed in a sterilization chamber 50. The sealed pouch 54 has gas diversion panel walls 55, 56 sealed together with a filter vent 58 providing gas passageway between the pouch compartment 59 and external environment 60. The vent 58 serves multiple functions; initially, it provides a means for gas transfer into and out of the compartment 59 so that the compartment interior and its contents represented by the syringe 53 may be sterilized. In addition, after completion of sterilization, the vent provides a barrier to and/or filters out undesirable material e.g. particles, dust, bacteria, viruses, pathogens, etc. to permit the packaged good to be transported, stored and handled prior to use without compromising the sterility of its contents. It also permits the package to shipped or subjected to, or maintained in environments which have a wide range of pressures or pressure changes without damage to the package caused by pressure differentials between the exterior and interior of the package.

After introduction of the pouch to the chamber 50, the chamber is closed and the state of the atmosphere around the pouch 54 is as depicted by the closed headed arrows in FIG. 5, namely, the air flow is random with no pressure differential between the internal compartment 59 and the external environment 60 outside the pouch. Airflow in port 51 and out port 52 is in equilibrium. Then the sterilization process begins and the ingress port 51 is closed and a vacuum applied to the egress port 52. Since there are little or no restrictions between the external environment 60 and egress port 51 gases in the external environment air removed quickly. However, atmospheric gases contained within the interior compartment 59 of pouch 54 have no place to go except through the restricted passageway provided by the filter media of filter vent 58. Thus, depending upon the venting capability of the filter vent there will be a tendency for the pouch panel walls to expand, as shown in FIG. 6, due to a pressure differential that is formed between a low pressure zone in the external environment 60 and a relatively high pressure zone in the interior compartment 59 of pouch 54. If the pressure differential is too great and/or lasts for too much time, then this expansion balloons out the pouch thereby stressing the perimeter seals which may then lead to weakened seals which may prematurely fail and ultimately result in destruction of package integrity and sterility. As depicted by closed headed arrows in FIG. 6, the gases within the internal compartment can only flow out via the filter vent 58 unless the pouch wall ruptures or seals fail and burst open.

In the sterilization process, once the chamber and pouch contents have been evacuated, then the pressure is reversed, but with addition of a sterilizing gas which is typically ethylene oxide (ETO) and/or steam. The egress means represented by egress port 52 is closed and ETO and/or steam is admitted e.g. through ingress means represented by ingress port 51. The process is then repeated for a plurality of cycles depending upon the protocols for sterilization used by various manufacturers and packagers. Flushing gases such as nitrogen and also elevated humidity may be employed in these processes. The temperature employed during this process may also be varied to enhance or aid the sterilization process and typically elevated temperatures may be used, but decreased temperatures may also be used as well as a combination thereof. Thus, it may be seen that it is highly desirable to employ filter vents capable of quickly transporting large volumes of gas to minimize (i) pressure differential magnitude, and (ii) the length of time at a pressure differential. In addition to the stresses placed upon the container walls and seals, the time for the sterilization process is impacted because those stresses may be minimized by slowing the rate of change of the pressure or vacuum applied during the process as a means to avoid undue stress on the container. So if a vacuum is applied slowly i.e. with a slow ramp up in pressure, then more time is afforded to permit the passage of gas across the filter vent and this reduces both the pressure differential and stress at the expense of a slower sterilization process. It would be desirable to have a quick process and permit the sterilization equipment to sterilize more containers in a given amount of time.

Figures 7, 8:
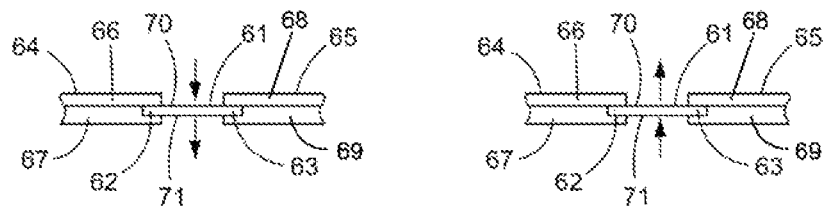
FIG. 7 is a schematic view of a section of pouch having a prior art filter vent showing gas flow across the vent thickness.
FIG. 8 is a schematic view of the pouch of FIG. 7 showing reversed direction air flow.

Referring now to FIGS. 7 and 8, schematic views of a section of a container pouch wall having a prior art filter vent 61 is depicted. The prior art filter vent 61 is provided as a strip of sheeting having a first end 62 and opposing second end 63. These ends 62 and 63 connect opposing sides of the filter vent 61 to first and second container wall panel segments 64 and 65. First end 62 is sealed between an outer layer 66 and inner layer 67 of a first wall segment 64. Second end 63 is sealed between outer layer 68 and inner layer 69 of second wall segment 65. The closed arrows indicate the flow of gas under pressure across the prior filter vent 61. This flow is from the outer surface 70 of the vent 61 across its thickness to the inner side 7l in FIG. 7 and the flow is reversed from the inner surface 71 to the outer surface 70 in FIG. 8. This prior art filter vent is typically a calendared medical grade paper or a calendared spun bonded polyolefin such as that commercially sold under the brand Tyvek. This spunbonded material is a very good barrier to passage of microbes and particulates, but requires a large surface area to provide sufficient gas flow across its thickness for efficient use in gas sterilization processes. Also the softening and melting point temperatures for spunbonded polyolefins used in commercial Tyvek® are such that heat seals to the material are weakened by exposure to steam heat leading to possible premature seal failure especially under the stresses produced by the inherent air flow restrictions of the material. Also, gas flow transverse to its thickness is inherently blocked by the structure of the commercial material forming an effective barrier to transverse venting. Typical thicknesses of commercially available spun bonded polyolefin materials used in sterilizable packaging range from about 6 to 7 mils (152-178μ). Papers are also sometimes used and have a thickness which ranges from 2 to 6 mils (51-152μ). Both papers and spunbonded polyolefins such as Tyvek® have significant resistance to transverse gas flow which is inadequate for any utility as a radial vent.

Figures 9, 10:
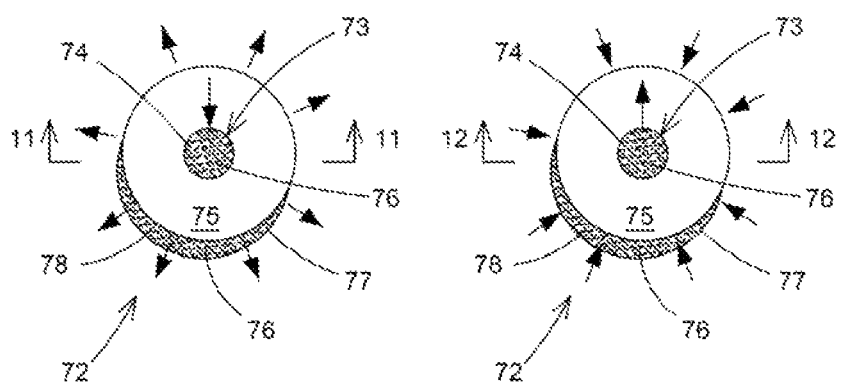
FIG. 9 is a schematic view of an embodiment of the invention showing air flow in one direction.
FIG. 10 is a schematic view of the embodiment of FIG. 9 showing reversed air flow.
Figure 11:
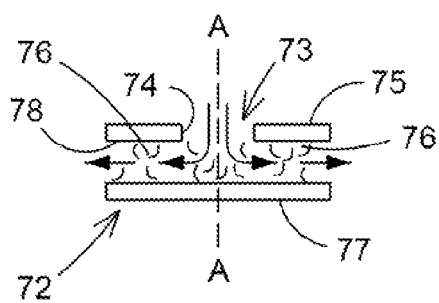
FIG. 11 is a sectional view taken along lines 11-11 of FIG. 9.
Figure 12:
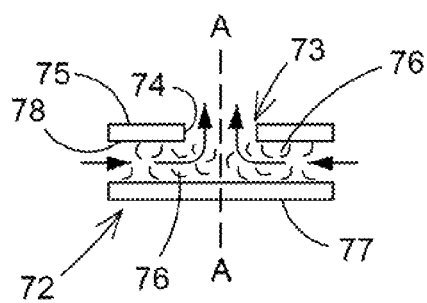
FIG. 12 is a sectional view taken along lines 12-12 of FIG. 10.
Figure 13:
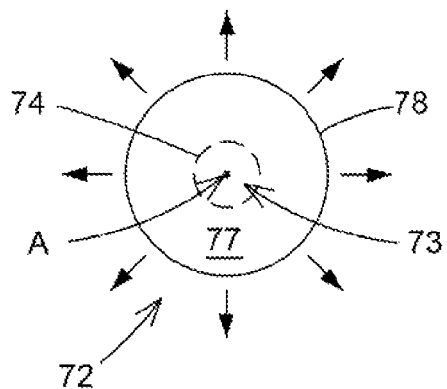
FIG. 13 is a schematic view of an opposite side of the vent of FIG. 9.
Figure 14:
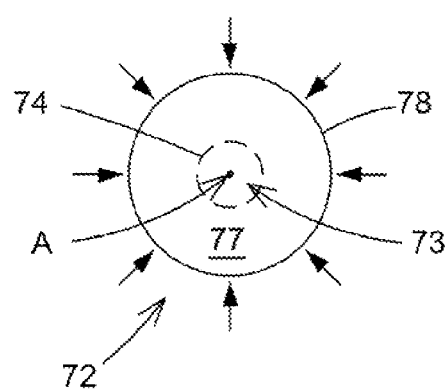
FIG. 14 is a schematic view of an opposite side of the vent of FIG. 10.

Returning to the invention, FIGS. 9-14 show how gases such as air, oxygen, nitrogen, and ethylene oxide flow in a radial filter vent 72 according to the present invention. FIGS. 9, 11 and 13 all use closed head arrows to show gas flow into a circular opening 73 having an opening perimeter 73 in a first diversion layer 75 and the gases proceed through a sheet of filter media 76 where the gas flow is blocked by a second gas diversion layer 77 and diverted through a tortuous path of the filter media to exit points at a perimeter edge 78 of the filter media 76. The air flow path also represents the tortuous path which blocks and filters out particulates and organisms. FIGS. 10, 12 and 14 all use closed head arrows to show the reversed direction gas flow into the perimeter edge 78 of the filter media 76 through a tortuous path of the filter media and out the circular opening 73 having an opening perimeter 73 in a first diversion layer 75.

The key parts of the radial filter vent according to the invention are: (1) a filter media, preferably in the form of a thin sheet or disc, that combines: (i) good gas flow (not only across its thickness, but transversely along its length and preferably radially in all directions) with (ii) excellent filtration barrier properties (to arrest, impede and bar transfer of undesired materials between the entrance and exit points of the filter media); (2) a first diversion layer that covers a desired portion of a filter media surface; and (3) a second diversion layer across the thickness of the filter media from the first diversion layer and having an opening therethrough. The position of the two gas diversion layers and opening are such that a longer transit path than the width of the filter media is formed. This longer transit path mainly extends radially or transversely to the shortest distance across the filter media thickness. In this manner a longer tortuous path may be utilized with a sufficiently open pore structure to preferably both increase gas flow and reduce undesired particle and material transmission between ingress and egress points. In prior art filter vents adapted for use in packaging such as flexible containers like pouches, bags, envelopes and the like, or with lid stock for semi-rigid or rigid containers such as trays, the venting and filtration is always across the thickness of the filter media which is typically paper or spun bonded polyolefin and especially that sold under the trademark Tyvek®. Tyvek® is an excellent barrier to transmission of undesired materials such as particulates and micro-organisms such as bacteria and viruses, but provision of this type of material barrier causes gas flow to be restricted. This gas flow restriction is ameliorated by using a sufficiently large area of filter media to reduce pressure differentials induced by expected conditions of use. However, use of large areas of e.g. Tyvek® increases cost and also presents an increase chance that fibers from the spunbonded filter media may detach and contaminate package contents. The present invention takes a different approach to address these limitations of the prior art. In the present invention a filter media having an open pored three dimensional tortuous path structure is utilized with gas diversion layers (which also are barriers to other materials including particulates, organisms, bacteria, viruses, etc.) to direct the flow of gases along a longer path than the thickness of a thin sheet material. In this manner several improvements and advantages over the prior art are enabled First, the possibility of contact between the contents and the filter media is reduced because a gas diversion layer may cover most, and preferably all, of the package interior filter sheet surface except for its sideways facing edge or a portion thereof. This diversion layer may be selected to not only to divert and restrict the flow of gas, but it may be impervious to gas transmission, and it may also be inert with respect to the package contents and act as a barrier to any other undesired material such as micro-organisms, bacteria, viruses, particulates, dust, etc., Advantageously, it may also be selected to present a smooth, nonabrasive surface which is unlikely to contaminate the contents e.g. by detached or abraded fibers or particles from a coating.

Second, a longer tortuous path may be used to provide excellent filtration while utilizing increased pore sizes. By appropriate selection of filter media and in conjunction with the diversion layers provided gases are directed lengthwise and radially from a center axis "A" as shown in FIGS. 11-14. The distance from the perimeter of the opening 74 and the barrier free filter edge perimeter 78 is greater than the filter thickness between the first and second diversion layers 75 and 77. By increasing the distance, filtration capability may be maintained or even improved while at the same time increasing pore size or passageway clearance; and this can be done while keeping a low profile along the package wall which minimizes the projection of the vent into the package interior. Thus the thickness of the vent 72 is kept small, typically sizes under 125 mils (3.2 mm) in thickness, and preferably from about 60 to 125 mils (1.5-3.2 mm). Depending upon the application the filter media sheet thickness may range as thin as is consistent with the volume of gas and gas flow rate that is needed for conditions of use. It is contemplated that thicknesses as low as 100 microns will be suitable. Of course larger thicknesses could be employed, but typically there will be no offsetting advantage to do so. By keeping the thickness low to provide a thin vent, the vent will not interfere with the package contents, content loading and removal with be unhindered and there will be less likelihood of abrasion or detachment by frictional forces. Also, more pouches may be held within a given unit space. This increase in gas passageway by providing a lateral path does not come at the expense of increased filter sheet sizes since the prior art commercial calendared paper and spun bonded polyolefin sheets already require a larger lateral area due to vent flow rate limitations inherent in those materials. Third, air flow rates are greatly improved by provision of filtration media that have larger pore sizes or gas passageway clearance, without sacrificing material, particulate and micro-organism filtration capabilities. The present invention utilizes three dimensional gas flow provided by open celled materials such as sintered open celled polymers and an open celled foamed polymers and plastics.

Thus, the present invention may see an improvement in one or more of the above properties. Preferred embodiments of the invention will have a combination of improved properties. The inventive radial filter vent and packaging may increase air flow rates while maintaining or increasing filtration against passage of unwanted materials while providing a protective filter cover on the package interior and do this in a smaller space and using less material than presently employed in commercial packaging e.g. for medical devices and supplies.

The radial filter vent may be provided as a unit as described above and with respect to FIGS. 9-14 for use by sealing e.g. by heat, adhesive, fusion, ultrasonic welding or otherwise to a flexible polymeric or plastic material such as a pouch, bag, rollstock for form-fill-seal equipment, lid stock, formed sheets with content cavities, or rigid containers or trays with rigid, semi-rigid or flexible tops. Suitable containers may utilize a variety of materials and combinations thereof including cellulosic and noncellulosic polymers, papers and nonwovens, flexible plastic films and sheets, metallized films, metal foils, etc.

Figure 15:
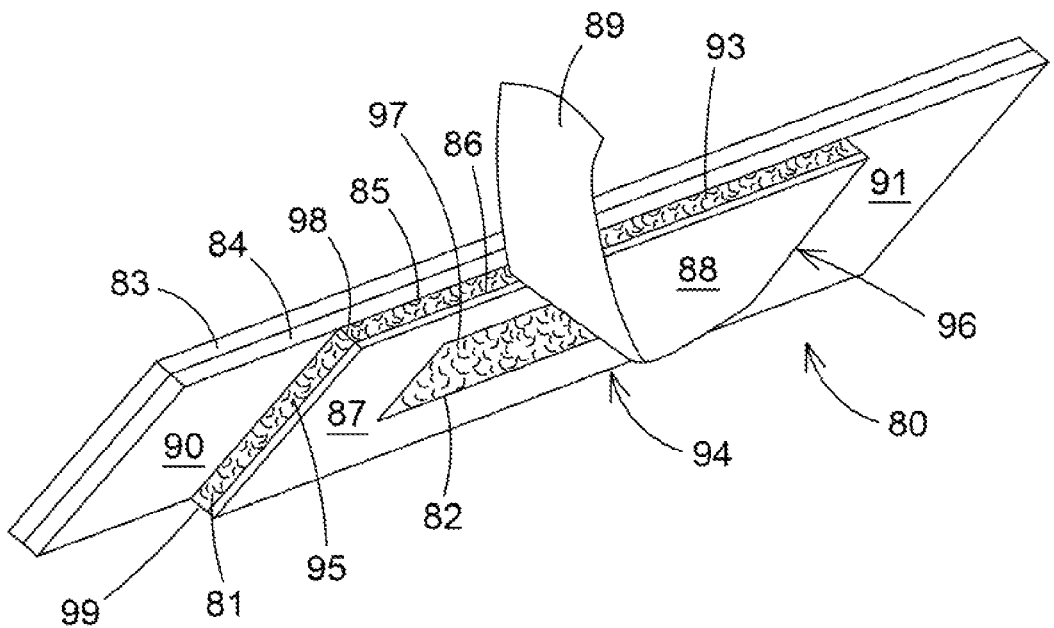
FIG. 15 is a schematic view of an alternative embodiment of the inventive radial filter vent.

Referring now to FIG. 15, an alternative embodiment of an inventive radial filter vent component 80 is depicted. In this embodiment of the invention the vent component is in adhesive strip form with a rectangular shaped sheet of filter media 81 and slot shaped gas access opening defined by rectangular perimeter 82. Vent 80 has a gas diversion layer 83 attached by adhesive layer 84, which may be a pressure sensitive adhesive, to filter media sheet 81 at a first filter media sheet surface 85. The filter media sheet 81 has an opposing second surface upon which is a pattern applied adhesive 87 with a rectangular adhesive free area which is also defined by rectangular perimeter 82. Thus the adhesive free area corresponds to the gas access opening and both have the same perimeter 82. A polymeric release liner 88 having a silicone release coating 89 is used to cover and protect the second adhesive coated filter surface and may be manually peeled back as depicted for removal. The adhesive layer 84 has first and second tab areas 90, 91 which may be similarly protected by release liners (not shown) until removal prior to attachment to a container wall (not shown). In applying the radial filter vent to a container wall, the adhesive free area 87 is aligned to overlap an opening in the container wall to provide gas communication therethrough. Gases passing through the vent would have access through this opening and also through lengthwise perimeter edges 93, 94, and optionally side perimeter edges 95, 96 of the rectangular filter media sheet 81. The adhesive tabs 90, 91 may be adapted to seal edges 95, 96 if desired. In this manner gas flow is communicated from a slot access edge e.g. at slot perimeter side 97 to a minimum distance to lengthwise perimeter edge 93 which will typically and preferably be longer than the thickness of the filter media from the shortest distance to or average distance between first surface 85 and second surface 86. Advantageously the tabs 90, 91 may be positioned within a package surface so that articles loaded into and removed from a container compartment would slide over the diversion layer opposite the tab portions and not get caught or abrade or come into contact with the filter media edges 95 or 96 which are protected by this positioning. Similarly the exposed lengthwise edges 93,94 are also protected by their orientation which is parallel to the direction of movement of insertion and removal and which also presents only a very small almost point like area of potential contact represented by the line where corner edges meet e.g. at 98, 99.

Figure 16:
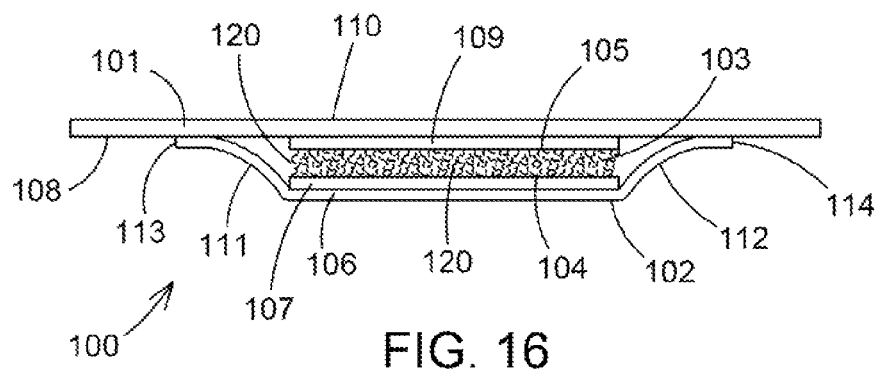
FIG. 16 is a sectional view of an alternative embodiment of the invention.
Figure 17:
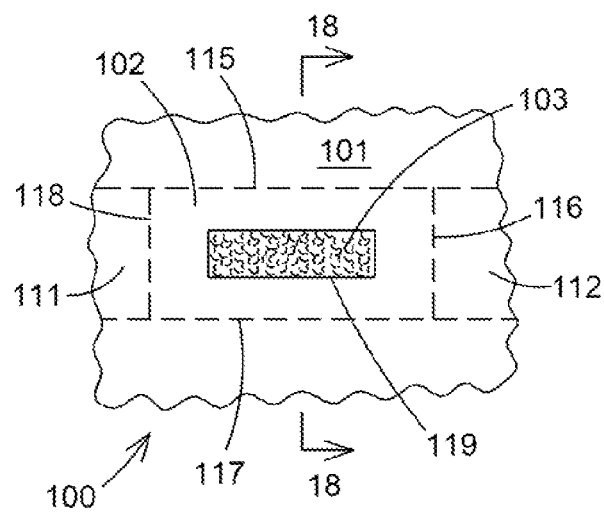
FIG. 17 is a schematic view of a container segment having a radial filter vent in accordance with the invention.
Figure 18:
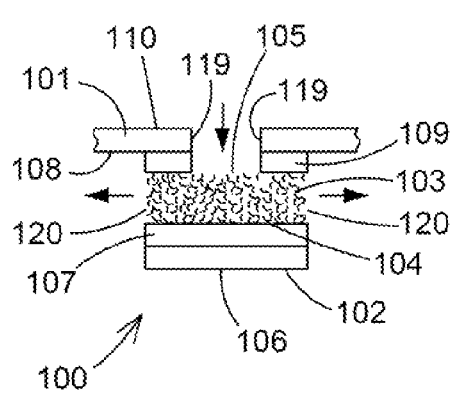
FIG. 18 is a sectional view of segment of FIG. 17 taken along lines 18-18.

Referring now to FIGS. 16-18, another embodiment of an inventive radial filter vent 100 is shown. This embodiment is very similar to that of FIG. 15 except no adhesive is used in the areas that correspond to tabs 90, 91 of FIG. 15, instead the polymeric gas diversion material is fused to the container wall by heat sealing or ultrasonic welding. In FIGS. 16-18 a container wall 101 has attached thereto a radial filter vent component 102 which comprises a rectangular thin sheet strip 103 of filter media having respective first and second sheet surfaces 104, 105 with a gas diversion layer 106 attached to the first filter media sheet surface 104 by first adhesive layer 107. The second filter media sheet surface 105 is attached to an interior surface 108 of container wall 101 by a second adhesive layer 109. The wall 101 has an opposing exterior surface 110. Gas diversion layer 106 has first and second tabs 111, 112 fused to the interior surface 108 to provide a radial filter vent 100 with respective seals 113, 114. The tabs 111, 112 provide a smooth surface over which product may be inserted into and removed from a container compartment while permitting unimpeded gas flow through a peripheral perimeter edge of the filter media sheet (as best shown in FIG. 18).

Referring now to FIG. 17, a section of the container wall 101 with attached vent component 102 is shown in schematic view from the point of view of the wall 101 exterior. An outline of the location of the attached filter media sheet is shown by rectangular dashed lines 115, 116, 117, 118 with portions of the first and second tabs 111, 112 also depicted with dashed line borders. A slot shaped opening defined by perimeter 119 provides gas access to the filter sheet 10.

Referring now to FIG. 18 a sectional view of the radial filter vent of FIG. 17 is shown taken along lines 18-18. Closed headed arrows show the direction of gas flowing through the opening defined by perimeter 119 in wall 101 and out of the filter media side edges 120 (see both FIGS. 16 and 18). Additional vent features shown in FIGS. 16 and 17 are likewise indicated here by the same reference numbers. Although one direction of gas flow is shown, in use it is expected that the pressure differential will be reversed to provide gas flow in the opposite direction as well as further described in this specification.

Figure 19:
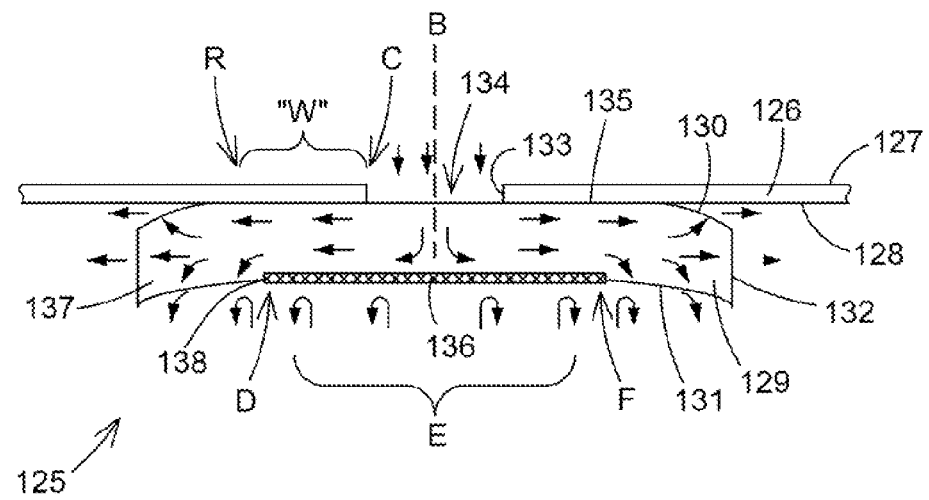
FIG. 19 is a schematic view of a section of an alternative embodiment of the inventive radial filter vent showing air flow.

Referring now to FIG. 19, yet another embodiment of the invention is shown. For the purpose of illustrating this embodiment assume that the section in view is the same as any section in rotation about an axis "B", but it will be apparent that other symmetrical and nonsymmetrical designs could be employed. A radial filter vent 125 is made in a package wall 126 having an exterior wall surface 127 and interior wall surface 128 by attaching an open pored polymeric filter sheet 129 having a first surface 130 and opposing second surface 131 and side edge 132 to wall 126 such that surface 130 of the filter sheet is sealed to the interior surface 128 of wall 126 adjacent to a perimeter 133 defining a circular opening 134 in the wall 126 to provide a sealed area 135 of defined width "W" surrounding the opening 134 to create a first gas diversion area. Width "W" extends from point "R" which is the distal end point from axis "B" to point "C" so that RC defines distance "W" and BC equals the radius of the opening 134. The vent has a gas diversion portion 136 on the second surface 131 of filter sheet 129 which extends over a portion corresponding to with "E" which extends from point "D" to "F". This gas diversion portion may be formed by completely fusing the surface 131 over the area defined by "E" or by occluding or otherwise sealing surface portion "E" with a gas diversion adhesive material or by sealing another layer of a gas diversion or gas barrier material thereto. It will be noted that the end portion 137 of the filter sheet 129 does not have a barrier or gas restriction layer on any side, thus as shown in FIG. 19 gas entering opening 134 is confined by the sealed portions "W" and "E" and flows out the non-barrier edges and both top and bottom end portions which are free of any gas diversion layer or gas flow restrictive surface treatment. It will be appreciated that the thickness "t" of the filter sheet 129 between sealed area 135 represented by "W" and gas diversion portion 136 represented by "E" will be shorter in length than the distance "W" or the distance from the opening perimeter 133 to any point lying on the edge 138 of the gas diversion layer such as point "D" or "F." Preferably the distance "E" will equal the sum of "2W" plus the diameter of the opening 134. The diameter is twice the radius which is the distance from the center axis B to the opening perimeter 133. While these relationships are illustrated for a circular opening and diversion layer construction, it will be appreciated that other configurations may also be made including polygons such as square or rectangular structures and that the important relationship is to construct the diversion layers to provide a tortuous path which is longer radially than the width so that an open pore structure may be employed to increase vent gas flow rates while increasing the tortuous path distance to maintain or improve filtration.

Figure 20:
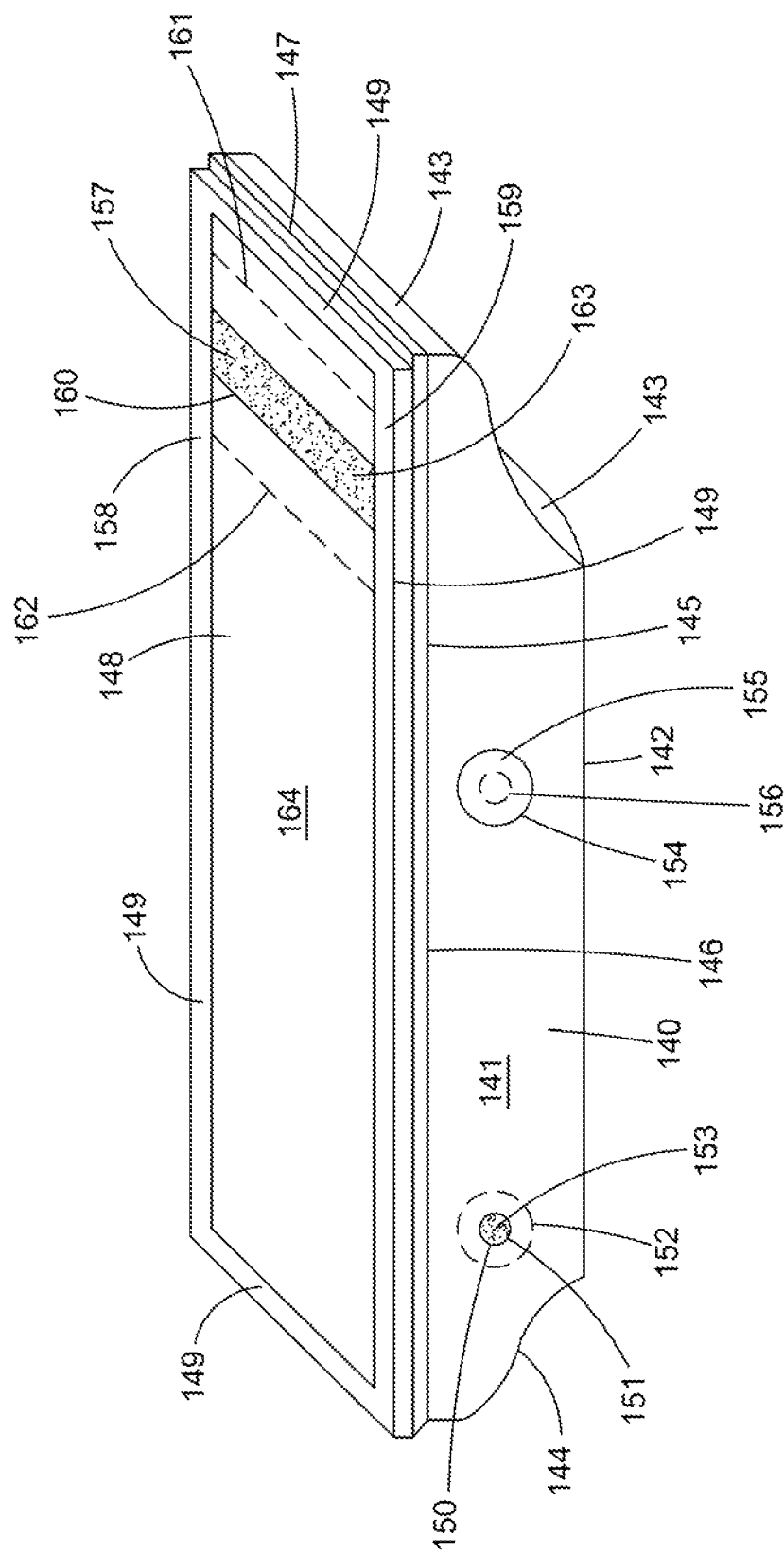
FIG. 20 is a schematic view of a lidded tray having a plurality of radial flow vents in accordance with the present invention.

Referring now to FIG. 20, a schematic view of a rigid tray 140 is depicted having a front side 141 and matching parallel rear side (not depicted) connected by an integral flat rectangular bottom panel having a front edge 142. The bottom panel is also integrally formed with an upwardly curved first end 143 and opposing similar upwardly curved second end 144. A top rectangular perimeter rim 145 lies in a plane and has front rim edge 146 which is connected to first tray end rim edge 147. The entire top rim is covered by a flexible lidstock 148 which is heat sealed to the rim 145 to form a top tray perimeter heat seal portion 149 which encloses the tray 140 and provides a barrier to particulates and other unwanted materials and organisms. Fluidic gaseous communication between an exterior environment and tray interior is provided by radial filter vents in accordance with the present invention and three embodiments are depicted. A first radial filter vent 150 is shown disposed and sealed within the tray to an interior wall surface of tray side 141. An opening in the front tray side wall 141 is defined by opening perimeter 151 and the interior outer perimeter of the vent 150 is shown by dashed circular line 152. Vent opening is covered on its interior by filter media 153. A similar second radial filter vent 154 is sealed to an exterior surface of the front tray side wall 141 and has a gas diversion layer 155 over filter media (not shown) and is positioned over an opening 156 in the front side wall 141 indicated by dashed line 156. Circular vents 150, 154 are similar in design to those depicted in FIGS. 1-4, and 9-14 and are illustrated here to show that radial filter vents according to the invention may be applied to either the interior or exterior of a container e.g. a tray. A third radial filter vent 157 is illustrated as a strip sealed to the interior surface of the lidstock 148 which extends from a rear portion 158 of perimeter seal 149 in the lidstock 148 to a front portion 159 of the heat seal 149. Vent 157 covers a slot shaped opening defined by a rectangular perimeter 160 and has interior opposing side edges 161 and 162 (shown in dashed lines) through which gas communicates with the opening 160 by passage through a tortuous path filter media 163. FIG. 20 also illustrates the efficiency of the filter vent 157 which could be used alone to provide a gas sterilization package. Filter vent 157 is a relatively small size whereas a prior art vent using e.g. a sheet of spunbonded polyolefin such as Tyvek® would cover a greater expanse, possibly the entire surface of the lidstock to achieve adequate gas flow across the Tyvek® sheet thickness. It will be appreciated that the inventive strip vent 157 is sealed to the lidstock to provide the desired gas passageway path length to capture undesirable materials, particulates, bacteria, viruses, organisms, etc. and may be of various shapes, sizes, lengths, widths and dimensions.

The containers e.g. a pouch can further include a tearing aid or tear initiator such as a notch. Examples of tearing aids or tear initiators such as notches, slits, perforations, surface roughened portions, etc., are described in U.S. Pat. Nos. 4,778,058; 3,608,815; 4,834,245; 4,903,841; 5,613,779; 5,988,489; 6,102,571; 6,106,448; 6,541,086; 7,470,062; and 7,481,581. Such tear initiators may be used on one or more edges of the inventive pouch and package.

Following are examples given to illustrate the invention, but these examples should not be taken as limiting the scope.

Example A

A highly permeable, relatively thick 1/16 inch thick sheet of sintered porous polyethylene with a reported average effective pore size of 15-45 micron is selected as a filter medium. This material is commercially available as Por-4900 from Porex of Fairburn, Ga. An adhesive such as a pressure sensitive adhesive (PSA) is pattern applied to a release liner and then laminated to the top face of the filter sheet, leaving circular areas without PSA which are ¼ inch in diameter. Adhesive is applied to the bottom face of the filter sheet and a non-porous gas diversion film such as 48 gauge oriented polyester is laminated thereto. The sheet web of radial vent material is cut to the desired size and dimension and four separate webs are created by die cutting into the gas diversion film and filter sheet circular shapes of 0.5, 0.75, 1.0 and 2.0 inch diameter. Each web is wound on a roll. Each roll of release liner with disks of radial filter vents is brought to a pouching machine with a label application system. Two rolls of pouch film web are placed on the machine and brought together to form heat sealed pouches. One of the pouch film webs is punched at regular controlled intervals to create a ¼ inch diameter open hole in the web. At each opening, a radial filter vent is applied in register so the opening of the pouch film aligns with the uncoated area of the top face of the vent. The PSA around the open area is placed in contact with the pouch film and creates a seal to prevent gas leakage between the vent and the pouch film. The second pouch film is then applied and heat sealed to the first pouch film and both sealed films severed from the web to form an individual pouch with the vent sealed to the first film and located between the two films and with the pouch having one open end available for product insertion. The three side sealed pouch is used to package a device by a manufacturer or packager who places a product in the pouch, completes the final seal and sterilizes with a gas sterilization process.

In Examples 1-21, the indicated filter media sheet was tested for gas flow properties using an air flow tester comprising: (1) a tubular inverted open can shaped flow chamber having an open lower end and sealed upper end and equipped on its side with a flow meter, valve and air supply, and (2) a tubular mounting base with both upper and lower ends open. The lower end is raised on feet to allow unrestricted flow of air out of the tester. The flow chamber and base were clamped together holding therebetween an interposed test plate filter media sheet holder. A series of test plates were used having circular openings of the indicated diameters for testing. These circular openings were each centered with respect to the axis of the tubular chamber and base. Upper and lower gasket seals were provided on either side of the test plate to ensure an airtight seal between the flow chamber, test plate and mounting base. The filter media sheets were either mounted directly on the housing using the gaskets to obtain the maximum area or were mounted to test plates using adhesive. Once each sample was clamped into position, the air supply was turned on and the air pressure was slowly increased to the desired set points. These set points were recorded and the air flow volume transferred across the filter media sample was measured over time and recorded. Air flow velocity was calculated from the air flow volume measurement. For all examples the reported thickness was noted and average gauge thickness reported. The opening diameter (D) and area (A) were also measured and calculated respectively. For Examples 6-21 a gas diversion layer of commercially available 48 mil oriented polyester film was attached by adhesive to one side of the filter media and the opposite side was adhesively mounted to the test plate with no adhesive applied to the area aligned with the circular test plate opening. The gas diversion layer was circular and coextensive with the filter media perimeter; the diameter was recorded. The filter media sheet being in the form of a disk, its edge area was calculated from the sheet thickness and perimeter. The ratio of the edge area to the circular opening on the face of the filter disk sheet opposite the gas divider later equipped side was calculated and is reported in the tables below. Also for all Examples the air velocity (AV) at 3 psi was normalized against the value of the filter media sheet of Example 2.

Examples 1-5

Control and Comparative Examples—Not of the Invention

Example 1 is a control where the air flow tester was operated without any filter media thereby providing unrestricted air flow through the apparatus.

Examples 2-5 all tested flow properties across the thickness of a filter sheet disk without any gas diversion layer opposite the chamber or test plate opening. These examples establish the gas flow properties across the thickness for each material tested.

Examples 2 and 3 are comparative examples—not of the invention. Example 2 and 3 tested flow properties of a commercially available spunbonded polyethylene sold by DuPont under the trademark Tyvek® 1073B. In Example 2 the Tyvek® 1073B was coated with a heat sealable porous ethylene polymer coating as is commonly done commercially for gas sterilization packaging. In Example 3 uncoated Tyvek® 1073B was tested. Uncoated Tyvek® is also used commercially.

Comparative Examples 4 and 5, as well as Examples 7-12 of the Invention, are commercially available sintered porous polyethylenes. The material of Comparative Example 4 and inventive examples 7-12 is sold under the trade name POR-4900 by Porex and has a reported average pore size of 15-45 microns and nominal thickness of 0.062 inches. Comparative Example 5 is sold under the trade name POR-7744 by Porex and has a reported average pore size of 10 microns and nominal thickness of 0.025 inches.

Examples 13-18 of the Invention all use a filter media of an open cell foamed polyurethane. This material has a reported nominal 90 pores per lineal inch structure and is available from UFP Technologies. It is believed to be a reticulated flexible open cell urethane foam.

Examples 19-21 of the Invention all use spirometer filter media which is commercially available from Creative Biomedics as the filter web employed in a filter sold under the trade name ClearAdvantage™ CBI 1501. It is believed to be a polypropylene fiber mat. Referring now to the Tables 1-4, the above filter materials and radial vent assemblies were tested for gas flow properties which are reported along with dimensional data and other information below.

TABLE 1

| EX. No. | FILTER MEDIA TYPE | AVG. GAUGE mil | OPENING D/A inches/in² | GAS DIV. LAYER diameter inches | EDGE AREA in² | AIR FLOW VOLUME (AFV) ft³/hr | | | | | EDGE AREA/ OPENING AREA RATIO |
|---|---|---|---|---|---|---|---|---|---|---|---|
| | | | | | | @ 1 psi | @ 2 psi | @ 3 psi | @ 4 psi | @ 5 psi | |
| 1 | None | NA | 0.25/0.049 | None | NA | 90 | 130 | 155 | 175 | >180 | NA |
| 2 | coated spunbonded PE | 7.8 | 3.94/12.2 | None | NA | 13 | 29.75 | 47.5 | 68.3 | 73.75 | NA |
| 3 | uncoated spunbonded PE | 7.3 | 3.94/12.2 | None | NA | 25.5 | 54.5 | 80 | 98.3 | 117 | NA |
| 4 | sintered porous PE | 62 | 0.49/0.19 | None | NA | 55 | 80 | 105 | 125 | 142 | NA |
| 5 | sintered porous PE | 25 | 0.49/0.19 | None | NA | 22 | 50 | 70 | 85 | 105 | NA |
| 6 | uncoated spunbonded PE | 7.3 | 0.25/0.049 | 0.50 | 0.011 | 0 | 0 | 0 | 0 | 0 | 0.22 |
| 7 | sintered porous PE | 62 | 0.125/0.0123 | 0.625 | 0.12 | 0 | 0 | 6 | 10 | 12 | 9.8 |
| 8 | sintered porous PE | 62 | 0.125/0.0123 | 0.75 | 0.15 | 0 | 0 | 4 | 10 | 12 | 12 |
| 9 | sintered porous PE | 62 | 0.25/0.0123 | 0.50 | 0.10 | 6 | 12 | 18 | 25 | 35 | 8.1 |
| 10 | sintered porous PE | 62 | 0.25/0.0123 | 0.75 | 0.15 | 0 | 6 | 8 | 18 | 20 | 12 |
| 11 | sintered porous PE | 62 | 0.25/0.0123 | 1.0 | 0.19 | 0 | 6 | 8 | 15 | 18 | 15 |
| 12 | sintered porous PE | 62 | 0.50/0.20 | 1.0 | 0.19 | 0 | 15 | 20 | 30 | 40 | 0.95 |

NA = Not Applicable
ND = Not Determined

TABLE 2

| EX. No. | FILTER MEDIA TYPE | AVG. GAUGE mil | OPENING D/A inches/in² | GAS DIV. LAYER diameter inches | EDGE AREA in² | AIR FLOW VELOCITY (AV) ft/min | | | | | AV @ 3 psi relative to EX. 2 |
|---|---|---|---|---|---|---|---|---|---|---|---|
| | | | | | | @ 1 psi | @ 2 psi | @ 3 psi | @ 4 psi | @ 5 psi | |
| 1 | None | NA | 0.25/0.049 | None | NA | 4500 | 6460 | 7700 | 8700 | ND | 822 |
| 2 | coated spunbonded PE | 7.8 | 3.94/12.2 | None | NA | 2.6 | 5.87 | 9.37 | 13.5 | 14.6 | 1.00 |
| 3 | uncoated spunbonded PE | 7.3 | 3.94/12.2 | None | NA | 5.0 | 10.8 | 16 | 19.4 | 23.1 | 1.7 |
| 4 | sintered porous PE | 62 | 0.49/0.19 | None | NA | 690 | 1000 | 1330 | 1580 | 1790 | 140 |
| 5 | sintered porous PE | 25 | 0.49/0.19 | None | NA | 280 | 630 | 880 | 1100 | 1330 | 94 |
| 6 | uncoated spunbonded PE | 7.3 | 0.25/0.049 | 0.50 | 0.011 | 0 | 0 | 0 | 0 | 0 | 0 |
| 7 | sintered porous PE | 62 | 0.125/0.0123 | 0.625 | 0.12 | 0 | 0 | 1000 | 2000 | 2300 | 100 |
| 8 | sintered porous PE | 62 | 0.125/0.0123 | 0.75 | 0.15 | 0 | 0 | 800 | 2000 | 2300 | 80 |
| 9 | sintered porous PE | 62 | 0.25/0.0123 | 0.50 | 0.10 | 300 | 590 | 880 | 1200 | 1700 | 94 |
| 10 | sintered porous PE | 62 | 0.25/0.0123 | 0.75 | 0.15 | 0 | 300 | 400 | 880 | 980 | 40 |
| 11 | sintered porous PE | 62 | 0.25/0.0123 | 1.0 | 0.19 | 0 | 300 | 400 | 730 | 880 | 40 |
| 12 | sintered porous PE | 62 | 0.50/0.20 | 1.0 | 0.19 | 0 | 180 | 250 | 370 | 490 | 26 |

NA = Not Applicable
ND = Not Determined

TABLE 3

| EX. No. | FILTER MEDIA TYPE | AVG. GAUGE mil | OPENING D/A inches/in² | GAS DIV. LAYER Diameter inches | EDGE AREA in² | AIR FLOW VOLUME (AFV) ft³/hr | | | | | EDGE AREA/ OPENING AREA RATIO |
|---|---|---|---|---|---|---|---|---|---|---|---|
| | | | | | | @ 1 psi | @ 2 psi | @ 3 psi | @ 4 psi | @ 5 psi | |
| 13 | open cell foamed polyurethane | 60 | 0.25/0.049 | 0.50 | 0.094 | 50 | 80 | 105 | ND | ND | 1.9 |
| 14 | open cell foamed polyurethane | 60 | 0.25/0.049 | 1.0 | 0.19 | 60 | 85 | 120 | 160 | ND | 3.9 |
| 15 | open cell foamed polyurethane | 60 | 0.25/0.049 | 2.0 | 0.38 | 60 | 80 | 105 | 130 | 160 | 7.8 |
| 16 | open cell foamed polyurethane | 125 | 0.25/0.049 | 0.50 | 0.20 | 70 | 100 | 130 | 150 | ND | 4.1 |
| 17 | open cell foamed polyurethane | 125 | 0.25/0.049 | 1.0 | 0.39 | 75 | 110 | 120 | 140 | 155 | 8.0 |
| 18 | open cell foamed polyurethane | 125 | 0.25/0.049 | 2.0 | 0.79 | 75 | 110 | 135 | 155 | 175 | 16 |
| 19 | polypropylene fiber mat | 62.5 | 0.25/0.049 | 0.50 | 0.098 | ND | ND | 75 | ND | ND | 2.0 |
| 20 | polypropylene fiber mat | 62.5 | 0.25/0.049 | 1.0 | 0.20 | ND | ND | 75 | ND | ND | 4.1 |
| 21 | polypropylene fiber mat | 62.5 | 0.25/0.049 | 2.0 | 0.39 | ND | ND | 70 | ND | ND | 8.0 |

NA = Not Applicable
ND = Not Determined

TABLE 4

| EX. No. | FILTER MEDIA TYPE | AVG. GAUGE mil | OPENING D/A inches/in² | GAS DIV. LAYER diameter inches | EDGE AREA in² | AIR FLOW VELOCITY (AV) ft/min | | | | | AV @ 3 psi relative to EX. 2 |
|---|---|---|---|---|---|---|---|---|---|---|---|
| | | | | | | @ 1 psi | @ 2 psi | @ 3 psi | @ 4 psi | @ 5 psi | |
| 13 | open cell foamed polyurethane | 60 | 0.25/0.049 | 0.50 | 0.094 | 2400 | 3900 | 5140 | ND | ND | 548 |
| 14 | open cell foamed polyurethane | 60 | 0.25/0.049 | 1.0 | 0.19 | 2900 | 4200 | 5870 | 7830 | ND | 627 |
| 15 | open cell foamed polyurethane | 60 | 0.25/0.049 | 2.0 | 0.38 | 2900 | 3900 | 5140 | 6360 | 7830 | 548 |
| 16 | open cell foamed polyurethane | 125 | 0.25/0.049 | 0.50 | 0.20 | 3400 | 4890 | 6360 | 7340 | ND | 679 |
| 17 | open cell foamed polyurethane | 125 | 0.25/0.049 | 1.0 | 0.39 | 3700 | 5380 | 5870 | 6850 | 7580 | 627 |
| 18 | open cell foamed polyurethane | 125 | 0.25/0.049 | 2.0 | 0.79 | 3700 | 5380 | 6600 | 7580 | 8560 | 705 |
| 19 | polypropylene fiber mat | 62.5 | 0.25/0.049 | 0.50 | 0.098 | ND | ND | 3700 | ND | ND | 390 |
| 20 | polypropylene fiber mat | 62.5 | 0.25/0.049 | 1.0 | 0.20 | ND | ND | 3700 | ND | ND | 390 |
| 21 | polypropylene fiber mat | 62.5 | 0.25/0.049 | 2.0 | 0.39 | ND | ND | 3400 | ND | ND | 370 |

NA = Not Applicable
ND = Not Determined

As demonstrated by the results seen in the Table 1, the spunbonded polyethylene (PE) Tyvek® of Examples 2 and 3 both had air flow volumes in the range of about 25 to 100 ft³/hour across its thickness over about 12 square inches of material. In comparison, the sintered porous polyethylene had air flow volumes which ranged from 22 to 142 over a much smaller area of 0.19 square inches. Thus on a per unit area basis, the sintered materials from Porex were much more porous. This is further seen by the calculated values for air flow velocity reported in Table 2. The control had air flow velocities which ranged from 4500 to in excess of 8700 over the pressures tested. The volume of air flow at 5 psi was too great to be measured on the tester, but would have resulted in a higher air flow velocity than that reported at the 4 psi test condition. The velocities for the Tyvek® samples were low in the range of about 5 to 23 for uncoated Tyvek® and from about 2.6 to 14.6 for coated Tyvek®. It is noted that coating Tyvek® reduces the air flow by about 50%, but coated Tyvek® is highly desired to improve heat sealability. In comparison, in Examples 4 and 5 the sintered Porex material had airflows which ranged from 280 to 1790 feet per minute. As reported in the last column of Table 2, these air velocity values were normalized against the value for coated Tyvek® Example 2 and the Porex materials had velocities that were 94 to 140 times greater than Tyvek®. These foregoing tests were performed to demonstrate the inherent air flow properties of the material if used in a traditional manner where air flow is across the thickness of the filter sheet i.e. transverse to the plane of the sheet when laid flat.

In Example 5, the more porous uncoated Tyvek® was tested for radial air flow by attaching a Tyvek® disc having a 48 mil thick oriented polyester film gas diversion layer adhesively sealed to one side with the other side adhesively attached to a test plate having a ¼ inch diameter opening. In effect a radial filter vent is constructed, using the commercially available material typically employed for gas sterilization packaging. As seen by the reported test results, the air volume which transited radially was not significant at any of the tested pressures. The tested Tyvek® sheet disc was not porous in a transverse direction to its thickness and no measurable airflow was found. It is seen that calendared spunbonded polyolefin sheets such as Tyvek® typically used for gas sterilization packaging are not three dimensionally porous to gas flow. To lack three dimensional gas porosity is not to say that no gas permeation occurs, it means that any gas permeation along the plane e.g. of flat laid Tyvek®, is too slow in volume and velocity to find any meaningful use in a radial filter vent designed for typical gas sterilization processes or for pressure changes encountered in package transit e.g. over mountains.

In Examples 7-12 a series of radial filter vents were tested for gas flow properties. All used polyester gas diversion layers as described above and metal test plates having centered openings of various sizes. The porous sintered polyethylene was POR-4900 as sheet discs having the indicated dimensions. The reported test results and calculated velocity values show that air flow volumes and velocities demonstrate three dimensional porosity with gas passage through a filter sheet face with transverse diversion and gas passage through a peripheral edge of the filter media. Thus gas may transit between the edge and face of the filter sheet with flow resulting in a change of direction from an axial entrance point to a perpendicular exit point thus making a right angle or 90° turn in general direction from the typical across thickness flow in prior art packaging. The distances employed from the facial circular opening perimeter edge to an exit point at the filter media edge ranged from 0.125 inches to 0.375 inches compared to a filter sheet disc thickness of 0.062 inches. In comparison to the typical commercially used uncoated and coated Tyvek® thickness which range from about 0.0073 to 0.0078 inches or medical papers which are even thinner in thickness, typically between about 0.0025 and 0.0045 inches, it is seen that these examples of the invention provide a much greater distance of passage from entrance to exit points. This distance in the examples is generally about 16 to 48 times greater than the thickness of coated Tyvek® and even greater when compared to the thinner uncoated Tyvek® or medical currently papers used. This the present invention creates a device which may produce a longer path to intercept or otherwise filter out unwanted materials, microbes, viruses, bacteria, particulates, etc.

In the present invention the distance between gas entrance and exit points of the vent is greater than the thickness of the filter material used. As used herein it will be appreciated that it is contemplated that the entrance and exit point swill be reversible and flow will typically proceed back and fore e.g. in gas sterilization processes where vacuum is applied and then a sterilant gas pumped in followed by vacuum removal for several iterations followed by flushing cycles of vacuum purging and flushing gas to remove the sterilant gases. Any description with respect to entrance and exit should be read to include flow in the reverse direction unless otherwise specially excluded. Typically this distance will be at least double the distance, and may be 3, 4, 5, 6, 7, 8, 9, 10 or more times as great. This distance may be calculated e.g. for a circular radial filter vent e.g. by taking the gas diversion barrier dimension and subtracting the facial opening dimension and dividing by two. In Examples 7-12 this distance is calculated to be from 2 to 6 times greater in distance than the thickness of the filter media used and over 16 times greater than the thickness of commercially available coated Tyvek®. It is from 28 to 50 to 83 to 150 times greater than the thicknesses of commercially available papers for gas sterilization packaging. Suitable distance for the gas passageway in the radial filter vents of the present invention will be greater than 10 mil (0.010 inch) and typically greater than 50 mil (0.050 inch), preferably greater than 100 mil (0.100 inch), more preferably at least 250 mil. As this distance increases a longer tortuous path for filtration is presented with all the advantages presented by greater filtration. Balanced against an increased tortuous path will be the gas flow properties which as described above must be sufficient to withstand the pressure changes to which the package or other article will be subjected. The upper limits may be experimentally determined without undue experimentation based upon other parameters selected including usage environments e.g. gas sterilization apparatus and processes, transit conditions, and gas flow rates obtainable by different filter media, volumes to be sterilized or held, etc.

Examples 13-18 are of the invention and all were all conducted as for the examples 7-12 except that a different filter media was used viz an open pored, open cell foamed polyurethane as further defined above. Excellent three dimension porosity is demonstrated with high air flow volumes and velocities.

Examples 19-21 are of the invention and all were all conducted as for the examples 7-18 except that a different filter media was used viz a polypropylene fiber mat as further defined above. Excellent three dimension porosity is demonstrated with high air flow volumes and velocities.

Examples 22-25 are of the invention and results are reported in Table 5. For these tests, pouches were made from a multilayer polyester pouch film having ethylene polymer sealant layer, the pouch having dimensions of 6¼" long by 3³⁄₁₆" wide with a chevron seal. Each pouch had a hole made by using round punches of the indicated size. Next, the hole was covered with porous filter media sheet material attached to the film outer surface with 2 sided adhesive tape. Next, a 20 ml syringe was placed in each pouch and the pouches were sealed at the bottom using an impulse sealer. The pouches were run through a standard gas sterilization process using ethylene oxide (ETO). First a conditioning phase was run followed by an ETO exposure phase and an aeration phase to remove the ETO. The conditions for these phases are as follows:

Conditioning Phase:
Temperature: 54.0° C.
Initial Vacuum: 1.0 pounds per square inch absolute (psia)
Humidity Set Point: 2.3 psia
Relative Humidity (RH): 60%
Steam Dwell Time: 60 minutes
Vacuum Ramp Rate: 1.0 psia/minute
EO Exposure Phase:
Gas Type: 100% EO
Temperature: 54.0° C.
EO Concentration: 600 mg/L
Sterilant Set Point: 7.7 psia
EO Gas Dwell Time: 240 minutes
Vacuum Ramp Rate: 1.0 psia/minute
Aeration Phase:
Temperature: 55±4° C.
Time: 24 hours 40 minutes After sterilization, pouches were inspected for signs of seal creep. All pouches with seal failure were then excluded from the rest of the testing. Finally, the pouches were exposed to microbes using a full package exposure test method. The syringe was removed from each pouch and incubated in a growth medium to test for microbial contamination.

TABLE 5

| EX. No. | FILTER MEDIA TYPE | AVG. GAUGE mil | OPENING D/A inches/in$^2$ | GAS DIV. LAYER diameter inches | EDGE AREA in$^2$ | ETO CYCLES % Pass | Microbe Test % Pass |
|---|---|---|---|---|---|---|---|
| 22 | sintered porous PE | 62 | 0.125/0.0123 | 0.50 | 0.097 | 3/3 | 3/3 |
| 23 | sintered porous PE | 62 | 0.25/0.0123 | 0.50 | 0.10 | 5/5 | 5/5 |
| 24 | sintered porous PE | 62 | 0.25/0.0123 | 0.75 | 0.15 | 2/3 | 2/2 |
| 25 | sintered porous PE | 62 | 0.25/0.0123 | 1.0 | 0.19 | 2/3 | 2/2 |

The results of the tests show that all of the films had a sufficient microbial barrier. Also, even using a very small surface area with an opening no larger than ¼ inch the radial vented pouches of Examples 22 and 23 all passed gas sterilization without seal failure. The films of Examples 24 and 25 had only one failure each in the gas sterilization testing. It is believed that these failures were due to the gas pressure stresses created as the restrictions of the tortuous path distance increased from the opening perimeter to the radial filter edge relative to the vents of Examples 22 and 23. For Examples 22-25, these distances were ⅜, ¼, ½, ¾ inch respectively. These stresses could be relieved by providing a slightly thicker filter media sheet disk or by decreasing the distance e.g. by increasing the opening diameter.

These examples are not exhaustive and other features and properties of the other pouches illustrated herein in the Figures can be applied.

The present invention in its various embodiments finds particular utility in providing packaging for a product which undergoes gas sterilization such as a catheter.

The features of these embodiments illustrate that a variety of shapes, sizes and configurations may be employed in the present invention using non-peelable or peelable polymeric films with or without metal foil layers or tear initiators.

Advantageously, the present invention permits smaller sized filter vents to be used at a material cost savings while maintaining and enhancing protection of enclosed products from damage and contamination during transportation through zones of pressure differentials such as those found in gas sterilization operations.

In one embodiment of the invention, a gas sterilization package component includes a gas diversion wall stock for at least a portion of a container, where the wall stock has an opening therethrough. The gas sterilization package component also includes a gas diversion layer. In addition, the gas sterilization package component has a filter sheet disposed between the gas diversion wall stock and the gas diversion layer. Suitably, the filter sheet has a first surface and an opposing second surface circumscribed by a perimeter edge. Desirably, the first surface of the filter sheet is attached to a surface of the gas diversion layer, and the second surface of the filter sheet is sealed to a surface of the wall stock such that an opening in the wall stock is covered by the filter sheet. Furthermore, a gas passageway is defined from the opening through a portion of the second surface of the filter sheet, extending through the filter perimeter edge, or a distal portal area, of the filter sheet.

In another embodiment of the invention, a radial filter vent includes a first gas diversion layer having an opening therethrough, a second gas diversion layer, and a filter sheet disposed between the first gas diversion layer and the second gas diversion layer. Suitably, the filter sheet has a first surface and an opposing second surface circumscribed by a perimeter edge. Desirably, the first surface of the filter sheet is sealed to a first surface of the second gas diversion layer, and the second surface of the filter sheet is sealed to a first surface of the first gas diversion layer, such that an opening in the first gas diversion layer is covered by the filter sheet. Furthermore, a gas passageway is defined from the opening through a portion of the second surface of the filter sheet, extending through the filter perimeter edge, or a distal portal area, of the filter sheet.

In some aspects of this embodiment, the filter sheet is greater than 10 mil in thickness, such as greater than 100 mil in thickness.

In other aspects of this embodiment, the filter sheet has a gas passageway distance greater than a minimum thickness of the filter sheet.

In particular aspects, for example, the gas passageway can at least 10 mil in length, such as at least 25 mil in length, or at least 50 mil in length, or at least 100 mil in length, or even at least 200 mil in length.

In still other aspects of this embodiment, at least one of the gas diversion layers is a nonporous polymeric film or sheet.

In yet other aspects of this embodiment, at least one of the gas diversion layers is polyester, polyolefin, polyethylene, metal foil, spunbonded polyolefin, or an adhesive.

In still other aspects of this embodiment, the filter sheet comprises a material which has a portion of at least one surface fused to form at least one of the gas diversion layers.

In yet other aspects of this embodiment, the filter sheet has a three dimensional open cell structure.

In still other aspects of this embodiment, the filter sheet comprises a sintered porous polyolefin.

In yet other aspects of this embodiment, the filter sheet comprises an open celled foamed polymer.

In still other aspects of this embodiment, the filter sheet comprises a fibrous polypropylene mat.

In yet other aspects of this embodiment, filter sheet comprises a sintered porous polyethylene.

In still other aspects of this embodiment, the filter sheet has a pore size between 1- and 500 microns, such as between 15 and 50 microns, and in some aspects the pores may extend in three dimensions.

In yet other aspects of this embodiment, the radial filter vent is attached to a flexible film package wall, a rigid tray, a lidstock, or a semi-rigid container.

In still other aspects of this embodiment, the filter sheet further comprises an anti-microbial agent.

In yet other aspects of this embodiment, the filter sheet further comprises first pressure sensitive layer between the first surface of the filter sheet and the first surface of the second gas diversion layer.

In still other aspects of this embodiment, the filter sheet further comprises a pressure sensitive layer between the second surface of the filter sheet and the first surface of the first gas diversion layer.

In another embodiment of the invention, a radial filter vent comprises a first gas diversion layer and a filter sheet that is sealed on its first side to the first gas diversion layer, where the filter sheet has a first surface and an opposing second surface circumscribed by a perimeter edge. The radial filter vent of this embodiment further comprises a pressure sensitive adhesive coating that may suitably be applied in a pattern onto the second side of the filter sheet. In some aspects, the adhesive coating may have an opening area which is adhesive free, circumscribed by adhesive, which can create a non-adhesive opening area. The radial filter vent of this embodiment further comprises a release liner attached to the pressure sensitive adhesive coating, suitably on a side that is opposite from the filter sheet. In some desirable aspects, the second surface of the filter sheet is adapted for sealable attachment to a first surface of a second gas diversion layer, such that an opening in the gas diversion layer is covered by the non-adhesive opening area of the filter sheet and a gas passageway is defined from the opening area through a portion of the second surface of the filter sheet, which can desirably extend through the filter perimeter edge, or a distal portal area, of the filter sheet.

Various embodiments have been described above. Although the invention has been described with reference to these specific embodiments, the descriptions are intended to be illustrative and are not intended to be limiting. Various modifications and applications may occur to those skilled in the art without departing from the true spirit and scope of the invention as defined in the appended claims.

What is claimed is:

1. A gas sterilization package component comprising:
   (a) a gas diversion wall stock for at least a portion of a container, said wall stock having an opening therethrough;
   (b) a gas diversion layer;
   (c) a filter sheet disposed between (a) and (b), said filter sheet having a first surface and an opposing second surface circumscribed by a perimeter edge; wherein said first surface of said filter sheet is attached to a surface of said gas diversion layer and said second surface of the filter sheet is sealed to a surface of the wall stock whereby an opening in said wall stock is covered by said filter sheet and a gas passageway is defined from said opening through a portion of said second surface of said filter sheet and extending through said filter perimeter edge or a distal portal area of said filter sheet.

2. A radial filter vent comprising:
   (a) a first gas diversion layer having an opening therethrough;
   (b) a second gas diversion layer,
   (c) a filter sheet disposed between (a) and (b), said filter sheet having a first surface and an opposing second surface circumscribed by a perimeter edge; wherein said first surface of said filter sheet is sealed to a first surface of said second gas diversion layer and said second surface of the filter sheet is sealed to a first surface of said first gas diversion layer whereby an opening in said first gas diversion layer is covered by said filter sheet and a gas passageway is defined from said opening through a portion of said second surface of said filter sheet and extending through said filter perimeter edge or a distal portal area of said filter sheet.

3. A radial filter vent, as defined in claim 2, wherein said filter sheet is greater than 10 mil in thickness.

4. A radial filter vent, as defined in claim 2, wherein said filter sheet is greater than 100 mil in thickness.

5. A radial filter vent, as defined in claim 2, wherein said filter sheet has a gas passageway distance greater than a minimum thickness of said filter sheet.

6. A radial filter vent, as defined in claim 2, wherein said gas passageway is at least 10 mil in length.

7. A radial filter vent, as defined in claim 2, wherein said gas passageway is at least 25 mil in length.

8. A radial filter vent, as defined in claim 2, wherein said gas passageway is at least 50 mil in length.

9. A radial filter vent, as defined in claim 2, wherein said gas passageway is at least 100 mil in length.

10. A radial filter vent, as defined in claim 2, wherein said gas passageway is at least 200 mil in length.

11. A radial filter vent, as defined in claim 2, wherein at least one of said gas diversion layers is a nonporous polymeric film or sheet.

12. A radial filter vent, as defined in claim 2, wherein at least one of said gas diversion layers is polyester, polyolefin, polyethylene, metal foil, spunbonded polyolefin, or an adhesive.

13. A radial filter vent, as defined in claim 2, wherein said filter sheet comprises a material which has a portion of at least one surface fused to form sat least one of said gas diversion layers.

14. A radial filter vent, as defined in claim 2, wherein said filter sheet has a three dimensional open cell structure.

15. A radial filter vent, as defined in claim 2, wherein said filter sheet comprises a sintered porous polyolefin.

16. A radial filter vent, as defined in claim 2, wherein said filter sheet comprises an open celled foamed polymer.

17. A radial filter vent, as defined in claim 2, wherein said filter sheet comprises a fibrous polypropylene mat.

18. A radial filter vent, as defined in claim 2, wherein said fitter sheet comprises a sintered porous polyethylene.

19. A radial filter vent, as defined in claim 2, wherein said filter sheet has a pore size between 1-500 microns with pores extending in three dimensions.

20. A radial filter vent, as defined in claim 2, wherein said filter sheet has a pore size between 1-500 microns.

21. A radial filter vent, as defined in claim 2, wherein said filter sheet has a pore size between 15-50 microns.

22. A radial filter vent, as defined in claim 2, attached to a flexible film package wall, a rigid tray, a lidstock, or a semi-rigid container.

23. A radial filter vent, as defined in claim 2, wherein said filter sheet further comprises an anti-microbial agent.

24. A radial filter vent, as defined in claim 2, wherein said filter sheet further comprises a first pressure sensitive layer between said first surface of said filter sheet and said first surface of said second gas diversion layer.

25. A radial filter vent, as defined in claim 2, wherein said filter sheet further comprises a pressure sensitive layer between said second surface of said filter sheet and said first surface of said first gas diversion layer.

26. A radial filter vent comprising:
(a) a gas diversion layer;
(b) a filter sheet sealed on its first side to said gas diversion layer, said filter sheet having a first surface and an opposing second surface circumscribed by a perimeter edge;
(c) a pattern applied pressure sensitive adhesive coating on said second side of said filter sheet, said adhesive coating having an opening area which is adhesive free circumscribed by adhesive; and
(d) a release liner attached to said pressure sensitive adhesive coating on a side opposite from said filter sheet;

wherein said second surface of the filter sheet is adapted for sealable attachment to a first surface of a second gas diversion layer whereby an opening in said gas diversion layer is covered by said nonadhesive opening area of said filter sheet and a gas passageway is defined from said opening area through a portion of said second surface of said filter sheet and extending through said filter perimeter edge or a distal portal area of said filter sheet.

\* \* \* \* \*